US007177024B2

(12) United States Patent
Nilson et al.

(10) Patent No.: US 7,177,024 B2
(45) Date of Patent: *Feb. 13, 2007

(54) BOTTOM FLUORESCENCE ILLUMINATION ASSEMBLY FOR AN IMAGING APPARATUS

(75) Inventors: David Nilson, Walmut Creek, CA (US); Brad Rice, Danville, CA (US); Tamara Troy, Berkeley, CA (US)

(73) Assignee: Xenogen Corporation, Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/155,078

(22) Filed: Jun. 17, 2005

(65) Prior Publication Data

US 2005/0219535 A1 Oct. 6, 2005

Related U.S. Application Data

(63) Continuation of application No. 10/372,763, filed on Feb. 21, 2003, now Pat. No. 6,922,246, which is a continuation-in-part of application No. 10/189,886, filed on Jul. 3, 2002, now Pat. No. 6,894,289.

(60) Provisional application No. 60/359,663, filed on Feb. 22, 2002.

(51) Int. Cl.
*G01J 3/30* (2006.01)
*G01N 21/25* (2006.01)

(52) U.S. Cl. .................... 356/417; 356/317; 250/458.1

(58) Field of Classification Search ................ 356/317, 356/318, 417–419, 244, 246; 250/458.1, 250/459.1; 422/82.05, 82.08; 436/172
See application file for complete search history.

(56) References Cited

U.S. PATENT DOCUMENTS 3,871,767 A 3/1975 Holm-Hansen et al.

(Continued)

FOREIGN PATENT DOCUMENTS

EP 0493707 3/1996

(Continued)

OTHER PUBLICATIONS

Reichman, Jay, *Handbook of Optical Filters for Fluorescence Microscopy*, Chroma Technology Corp., pp. 1-37. Downloaded from www.chroma.com on Nov. 18, 2003.

(Continued)

*Primary Examiner*—Layla G. Lauchman
(74) *Attorney, Agent, or Firm*—Beyer Weaver & Thomas LLP

(57) ABSTRACT

A macroscopic fluorescence illumination assembly is provided for use with an a imaging apparatus with a light-tight imaging compartment. The imaging apparatus includes an interior wall defining a view port extending into the imaging compartment to enable viewing of a specimen contained therein. The illumination assembly includes a specimen support surface sized and dimensioned for receipt in the imaging compartment, and oriented to face toward the view port of the imaging apparatus. The support surface is substantially opaque and defines a window portion that enables the passage of light there through. The window portion is selectively sized and dimensioned such that the specimen, when supported atop the support surface, can be positioned and seated over the window portion in a manner forming a light-tight seal substantially there between. The illumination assembly further includes an excitation light source, and a bundle of fiber optic strands having proximal ends thereof in optical communication with the light source. The distal ends of the strands terminate proximate the window portion of the support surface. The distal ends each emit a respective beam of light originating from the light source which are then collectively directed toward the window portion and into a bottom side of the specimen wherein the diffused light passes there through and exits a topside thereof for receipt through the view port to view the fluorescence of the specimen.

16 Claims, 23 Drawing Sheets

U.S. PATENT DOCUMENTS

| | | | |
|---|---|---|---|
| 4,076,420 A * | 2/1978 | De Maeyer et al. | 356/73 |
| 4,582,406 A | 4/1986 | Wally | |
| 4,593,728 A | 6/1986 | Whitehead et al. | |
| 4,708,475 A * | 11/1987 | Watson | 356/417 |
| 4,863,690 A | 9/1989 | Berthold et al. | |
| 5,039,868 A | 8/1991 | Kobayashi et al. | |
| 5,202,091 A | 4/1993 | Lisenbee | |
| 5,319,209 A | 6/1994 | Miyakawa et al. | |
| 5,414,258 A | 5/1995 | Liang | |
| 5,542,012 A | 7/1996 | Fernandes et al. | |
| 5,636,299 A | 6/1997 | Bueno et al. | |
| 5,637,874 A | 6/1997 | Honzawa et al. | |
| 5,650,135 A | 7/1997 | Contag et al. | |
| 5,672,881 A | 9/1997 | Striepeke et al. | |
| 5,680,492 A | 10/1997 | Hopler et al. | |
| 5,705,807 A | 1/1998 | Throngnumchai | |
| 5,738,101 A | 4/1998 | Sappey | |
| 5,840,572 A | 11/1998 | Copeland et al. | |
| 5,867,250 A | 2/1999 | Baron | |
| 5,898,802 A | 4/1999 | Chen et al. | |
| 5,916,160 A | 6/1999 | Arcan et al. | |
| 5,970,164 A | 10/1999 | Bamberger | |
| 5,986,271 A | 11/1999 | Lazarev et al. | |
| 6,036,920 A | 3/2000 | Pantoliano et al. | |
| 6,043,506 A | 3/2000 | Heffelfinger et al. | |
| 6,071,748 A * | 6/2000 | Modlin et al. | 436/174 |
| 6,084,680 A | 7/2000 | Tuunanen et al. | |
| 6,097,025 A | 8/2000 | Modlin et al. | |
| 6,217,847 B1 | 4/2001 | Contag et al. | |
| 6,242,743 B1 | 6/2001 | DeVito et al. | |
| 6,321,111 B1 | 11/2001 | Perelman et al. | |
| 6,364,829 B1 | 4/2002 | Fulghum | |
| 6,510,281 B2 | 1/2003 | Schroder | |
| 6,597,864 B2 | 7/2003 | Schroder | |
| 6,615,063 B1 | 9/2003 | Ntziachristos | |
| 6,775,567 B2 | 8/2004 | Cable et al. | |
| 6,894,289 B2 | 5/2005 | Nilson et al. | |
| 6,901,279 B2 | 5/2005 | Cable et al. | |
| 6,922,246 B2 | 7/2005 | Nilson et al. | |
| 2001/0028510 A1 | 10/2001 | Ramm et al. | |

FOREIGN PATENT DOCUMENTS

| | | | |
|---|---|---|---|
| EP | 0718622 | 5/2003 | |
| WO | WO 99/08233 | 2/1999 | |
| WO | WO00/17643 | 3/2000 | |
| WO | WO 00/49938 | 8/2000 | |
| WO | WO00/50872 | 8/2000 | |
| WO | WO 01/61324 | 8/2001 | |
| WO | WO 01/63247 | 8/2001 | |

OTHER PUBLICATIONS

Yang, et al., *Whole-body optical imaging of green fluorescent protein-expressing tumors and metastases*, PNAS vol. 97, No. 3, Feb. 1, 2000.

Yang, et al., *Visualizing gene expression by whole-body fluorescence imaging*, PNAS vol. 97, No. 22, Oct. 24, 2000.

Hamamatsu Corporation, USA, website. http://usa.hamamatsu.com/ pp. 1-4, Apr. 27, 2001, printed on Apr. 27, 2001.

VetEquip Incorporated website, http://www.vetequip.com/1806.htm Table Top Laboratory Animal Anesthesia System, printed on Apr. 27, 2001.

VetEquip Incorpoated website, http://www.vegequip.com/1807.htm Mobile Laboratory Animal Anesthesia System, Apr. 27, 2001, printed on Apr. 27, 2001.

Hamamatsu, Imaging Box Instruction Manual, 55310-224-1, Nov. 2000.

Vet Equip Incorporated website, http://www.vetequip.com/impac. htm IMPAC$_6$ An anesthesia system designed for high volume, assembly-line type procedures, Apr. 27, 2001, printed on Apr. 27, 2001.

PCT/US01/06078, International Preliminary Exam Report mailed Dec. 9, 2002.

PCT/US01/06078, International Search Report mailed Feb. 23, 2001.

PCT/US01/06078, Written Opinion mailed Jun. 14, 2002.

Mahmood, et al., *Near-Infrared Optical Imaging of Protease Activity for Tumor Detection, Radiology*, Dec. 1999, pp. 866-870.

Weissleder, et al., *Shedding Light onto Live Molecular Targets, Nature Medicine*, vol. 9, No. 1, Jan. 2003, pp. 123-128.

PCT/US03/05199, Written Opinion mailed Nov. 12, 2003.

PCT/US03/05199, International Search Report mailed Oct. 12, 2003.

Australia application No. 2001241758, Examiner's First Report dated Nov. 18, 2004.

European Patent Application No. 03 713 577.9-2204, Examination report dated Feb. 20, 2006.

* cited by examiner

BOTTOM FLUORESCENCE ILLUMINATION ASSEMBLY FOR AN IMAGING APPARATUS

CROSS-REFERENCE TO RELATED APPLICATION

This application is a continuation of a U.S. Patent Application entitled "BOTTOM FLUORESCENCE ILLUMINATION ASSEMBLY FOR AN IMAGING APPARATUS" by Nilson et al., filed Feb. 21, 2003, U.S. application Ser. No. 10/372,763 now U.S. Pat. No. 6,922,246, which in turn is a continuation-in-part of a U.S. Patent Application entitled "FLUORESCENCE ILLUMINATION ASSEMBLY FOR AN IMAGING APPARATUS" by Nilson et al., filed Jul. 3, 2002, U.S. application Ser. No. 10/189,886, now issued as U.S. Pat. No. 6,894,289, which in turn claims priority under 35 U.S.C. 119(e) from U.S. Provisional Patent Application No. 60/359,663, entitled same and filed Feb. 22, 2002; all are incorporated herein by reference for all purposes.

TECHNICAL FIELD

The present invention relates generally to imaging systems, and more particularly, relates to macroscopic, bottom fluorescent illumination sources and their associated components to illuminate imaging systems.

BACKGROUND

One specialized type of imaging involves the capture of low intensity fluorescence. Briefly, fluorescence is a molecular phenomenon in which a substance absorbs light of a particular wavelength and emits light of a longer wavelength. The absorption of light is referred to as the "excitation", and the emission of longer wave lights as the "emission". Both organic and inorganic substances can exhibit fluorescent properties.

Fluorescence imaging is performed by illuminating a sample to excite fluorescence molecules in the sample, and then capturing an image of the sample as it fluoresces using a camera. Such imaging applications present particular challenges to the design of a box or chamber in which the sample is contained during imaging. This is especially true in macroscopic applications where the field-of-view is about 10 cm–30 cm in diameter, as compared to microscopic applications where the field-of-view is less than about 1 cm.

Typically, intensified or cooled charge-coupled device (CCD) cameras are used to detect the fluorescence of low intensity light radiating from the sample. These cameras are generally complex, may require specialized cooling, and are typically fixed to a single location on the top of a specimen chamber. A user places a sample at a predetermined position in the specimen chamber within the field of view for the overhead camera.

Due to this static design, one particular challenge to imaging apparatus design is the diverse lighting needs required during image capture. Fluorescent image capture, of course, involves the sample being illuminated with an in-box illumination source, while the minute amounts of fluoresced from the "excited" sample are detected using a light detector, e.g., a CCD camera.

One problem associated with the capture of overhead images in macroscopic applications is that the relatively large CCD camera is typically centrally located directly over the sample platform which supports the sample. A single illumination source is thus often positioned in the light box at a location off-set from the camera lens, and angularly directed at the sample platform. Thus, for relatively non-planar samples supported atop the platform, substantially uniform illumination is difficult to achieve. Such is also the case when multiple illumination sources are applied which often causes detrimental shadowing, and thus, non-uniform lighting.

Another problem associated with fluorescent imaging in macroscopic applications is that the current imaging apparatus generally employ dichroic mirrors to perform partial filtering functions. Briefly, dichroic mirrors are typically used in fluorescence microscopes to provide an additional amount of separation for the excitation and emission wavelengths. The dichroic mirror is usually mounted at about a 45 degree angle to excitation and emission light. The excitation light is reflected by the dichroic mirror onto the specimen, while the emission light passes through the dichroic mirror, the emission filter, the lens, and is incident on the CCD camera. Dichroic mirrors are commonly used on microscopes because the beam size is very small and so the mirrors are quite compact (usually 1 inch or less in diameter).

For a macroscopic application, as mentioned, the required field-of-view is much larger (i.e., 10 cm–30 cm) than that for a microscopic application (less than about 1 cm). This of course necessitates the use of a much larger lens which in turn renders the use of a dichroic mirror impractical. Due to the size and orientation of such a mirror in the imaging compartment of the imaging box, the footprint of the imaging box is unfeasibly large. In view of the foregoing, an improved illumination assembly for a light box that enables the substantially uniform lighting for fluorescent image capture of the sample would be highly desirable.

DISCLOSURE OF INVENTION

The present invention provides a macroscopic fluorescence illumination assembly for use with an imaging apparatus with a light-tight imaging compartment. The imaging apparatus includes an interior wall defining a view port extending into the imaging compartment to enable viewing of a specimen contained therein. The illumination assembly includes a specimen support surface sized and dimensioned for receipt in the imaging compartment, and oriented to face toward the view port of the imaging apparatus. The support surface is substantially opaque and defines a window portion that enables the passage of light there through. The window portion is selectively sized and dimensioned such that the specimen, when supported atop the support surface, can be positioned and seated over the window portion in a manner forming a light-tight seal substantially there between. The illumination assembly further includes an excitation light source, and a bundle of fiber optic strands having proximal ends thereof in optical communication with the light source. The distal ends of the strands terminate proximate the window portion of the support surface. The distal ends each emit a respective beam of light originating from the light source which are then collectively directed toward the window portion and into a bottom side of the specimen wherein the diffused light passes there through and exits a topside thereof for receipt through the view port to view the fluorescence of the specimen.

Accordingly, by illuminating the specimen through a bottom side illumination thereof with an excitation light source, as opposed to a topside illumination of the specimen, the autofluorescence background signal of the specimen itself is reduced. This is due to the fact that tissue autofluorescense is always higher on the side of the excitation light source than on the side facing the camera. In the case of a topside illumination, both the camera and the excitation light source are on the same side.

In one specific arrangement, a specimen illumination platform is provided including a cover plate that provides the support surface, and a support structure cooperating with the cover plate to define a light-tight interior cavity below the window portion. The distal ends of the fiber optic strands terminate in this cavity. The substantially parallel optical axes of the distal ends of the fiber optic are oriented in the cavity substantially perpendicular to a plane containing the window portion of the support surface. A reflector device is disposed in the cavity, and includes a substantially planar reflective surface oriented at an angle about 45° relative the direction substantially parallel to the optical axes of the distal ends of the fiber optic strands. In this orientation, the directional beams of light emitted from the fiber optic distal ends are reflected through the window portion and into the specimen. The distal ends of the fiber optic bundle are aligned in a linear array in another embodiment extending substantially along the elongated reflective surface.

The size window portion of the cover plate may be selected according to the specimen. It is preferably substantially rectangular shaped, and may be provided by a void in the cover plate or a transparent material.

In another configuration, a macroscopic fluorescence imaging assembly is provided for viewing a specimen. The imaging assembly includes an imaging apparatus having an enclosure wall defining a view port into a light-tight imaging compartment containing the specimen thereof, and a specimen illumination platform positioned in the imaging compartment having a support surface facing toward the view port. The support surface is substantially opaque and defines a window portion enabling the passage of light there through. The window portion is selectively sized and dimensioned such that the specimen, when supported atop the support surface, can be positioned and seated over the window portion in a manner forming a light-tight seal substantially there between. An illumination device is disposed in the imaging compartment below the specimen illumination platform and proximate the window portion of the support surface such that light emitted from the illumination device is directed toward the window portion and into a bottom side of the specimen wherein the diffused light exits a topside thereof for receipt through the view port to view the fluorescence of the specimen.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

BEST MODE OF CARRYING OUT THE INVENTION

Figure 1:
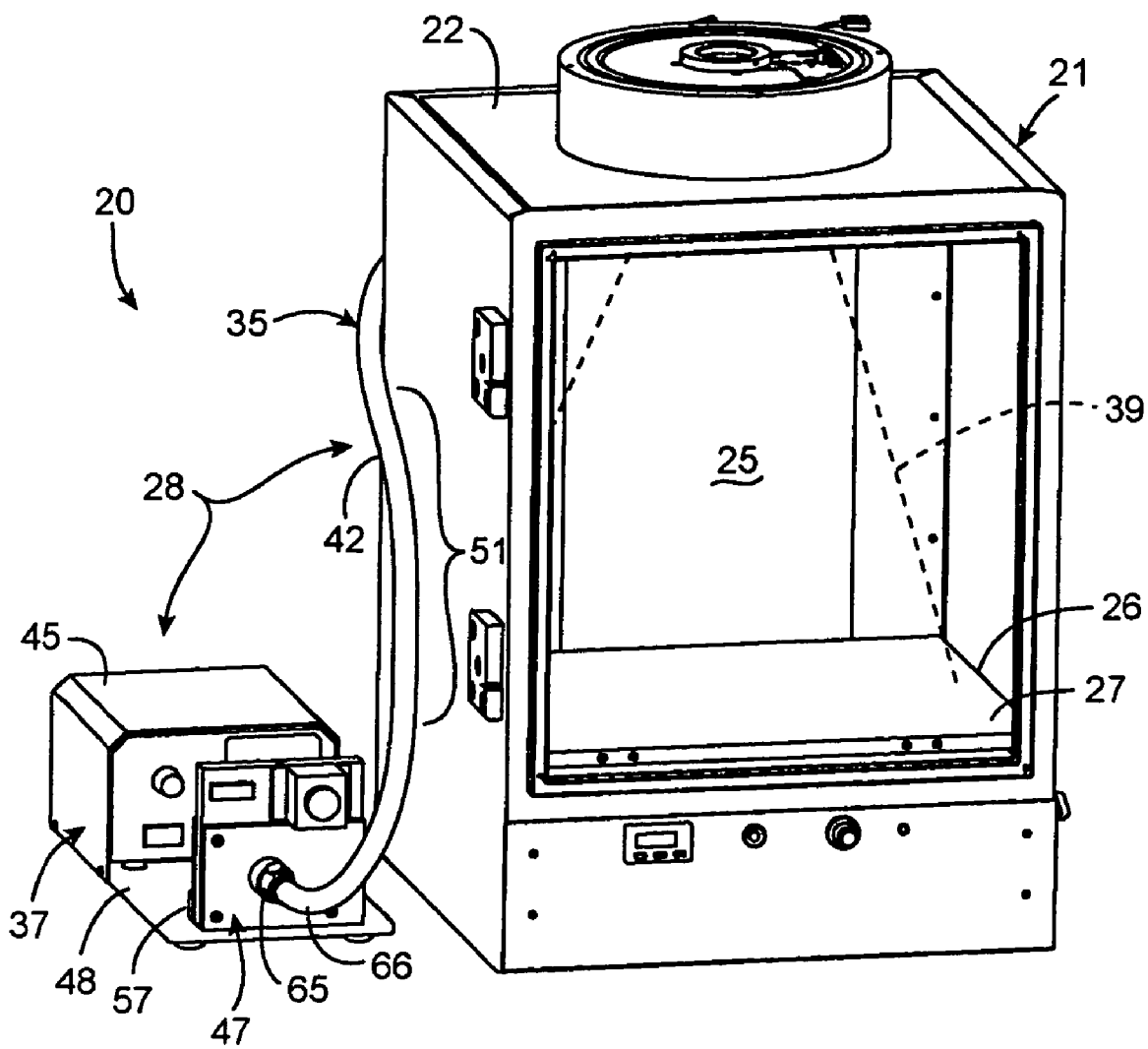
FIG. 1 is a top perspective view of an imaging apparatus, with the door removed, incorporating an illumination assembly constructed in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Referring now to FIGS. 1–5, a fluorescence imaging assembly, generally designated 20, is provided which includes a light-tight sample box or imaging apparatus 21 having an enclosure wall or upper housing 22 defining a view port 23 (FIG. 5) into a light-tight imaging compartment 25 thereof. A specimen platform 26 is positioned in the imaging compartment 25 which includes a support surface 27 facing toward the view port 23. The imaging assembly 20 further includes an illumination assembly, generally designated 28, having an illumination device 30 disposed in the imaging compartment 25, and positioned proximate to and substantially peripherally encircling the view port 23 such that said specimen platform 26 is illuminated in a substantially uniform manner.

Accordingly, by illuminating the specimen platform 26 from an illumination device peripherally extending around or continuously surrounding the camera view port 23, a specimen (not shown) positioned on the platform 26 will be substantially uniformly illuminated, symmetrically about the optical axis. Such uniform illumination is not attainable in the off-set lighting techniques currently applied without repositioning the lighting or the specimen.

Moreover, as will be apparent below, the improved filtering performance, the careful selection of low auto fluorescent materials for the filters and lighting components, as well as the formation of light tight seals essentially from the light source to the imaging compartment of the imaging apparatus, collectively enable sufficient filtered fluorescent lighting without the need for additional filtering through dichroic mirrors. Thus, in this macroscopic fluorescent imaging application, these relatively large dichroic filters can be eliminated. Consequently, the overall footprint of the imaging enclosure is substantially reduced.

Briefly, FIGS. 1–4 illustrate an imaging apparatus 21 suitable for capturing photographic, fluorescent or luminescence images in accordance with one embodiment of the present invention. The imaging apparatus 21 includes an upper housing 22 defining the view port in which a lens system of a high sensitivity camera 31 is mounted. This camera is preferably an intensified or cooled integrating Charge-Coupled Device (CCD) camera 31 which is positioned on top of the imaging apparatus 21 and positioned above the upper housing 22. The CCD camera 31 is capable of capturing fluorescent, luminescent and photographic (i.e., reflection based images) images of the sample within the imaging apparatus 21. The CCD camera 31 may be cooled by a suitable source such as a refrigeration device that cycles a cryogenic fluid through the CCD camera via conduits. A suitable refrigeration device is the "CRYOTIGER" compressor, which can be obtained from IGC-APD Cryogenics Inc., Allentown, Pa. Other methods, such as liquid nitrogen, may be used to cool the CCD camera 31.

An image processing unit optionally interfaces between camera 31 and a computer through cables. The computer, which may be of any suitable type, typically comprises a main unit that contains hardware including a processor, memory components such as random-access memory (RAM) and read-only memory (ROM), and disk drive components (e.g., hard drive, CD, floppy drive, etc.). The computer also includes a display and input devices such as a keyboard and mouse. The computer is in communication with various components in the imaging apparatus 21 via cable. To provide communication and control for these components, the computer includes suitable processing hardware and software configured to provide output for controlling any of the devices in the imaging apparatus 21. The processing hardware and software may include an I/O card, control logic for controlling any of the components of the imaging assembly 20, and a suitable graphical user interface for the imaging assembly 20. The computer may also include suitable processing hardware and software for the camera 31 such as additional imaging hardware, software, and image processing logic for processing information obtained by the camera 31. Components controlled by the computer may include the camera 31, the motors responsible for camera 31 focus, the motors responsible for position control of a platform supporting the sample, the camera lens, filter wheels, f-stop, etc. The logic in computer may take the form of software, hardware or a combination thereof. The computer also communicates with a display for presenting imaging information to the user. By way of example, the display may be a monitor, which presents an image measurement graphical user interface (GUI) that allows the user to view imaging results and also acts as an interface to control the imaging assembly 20.

Figure 2:
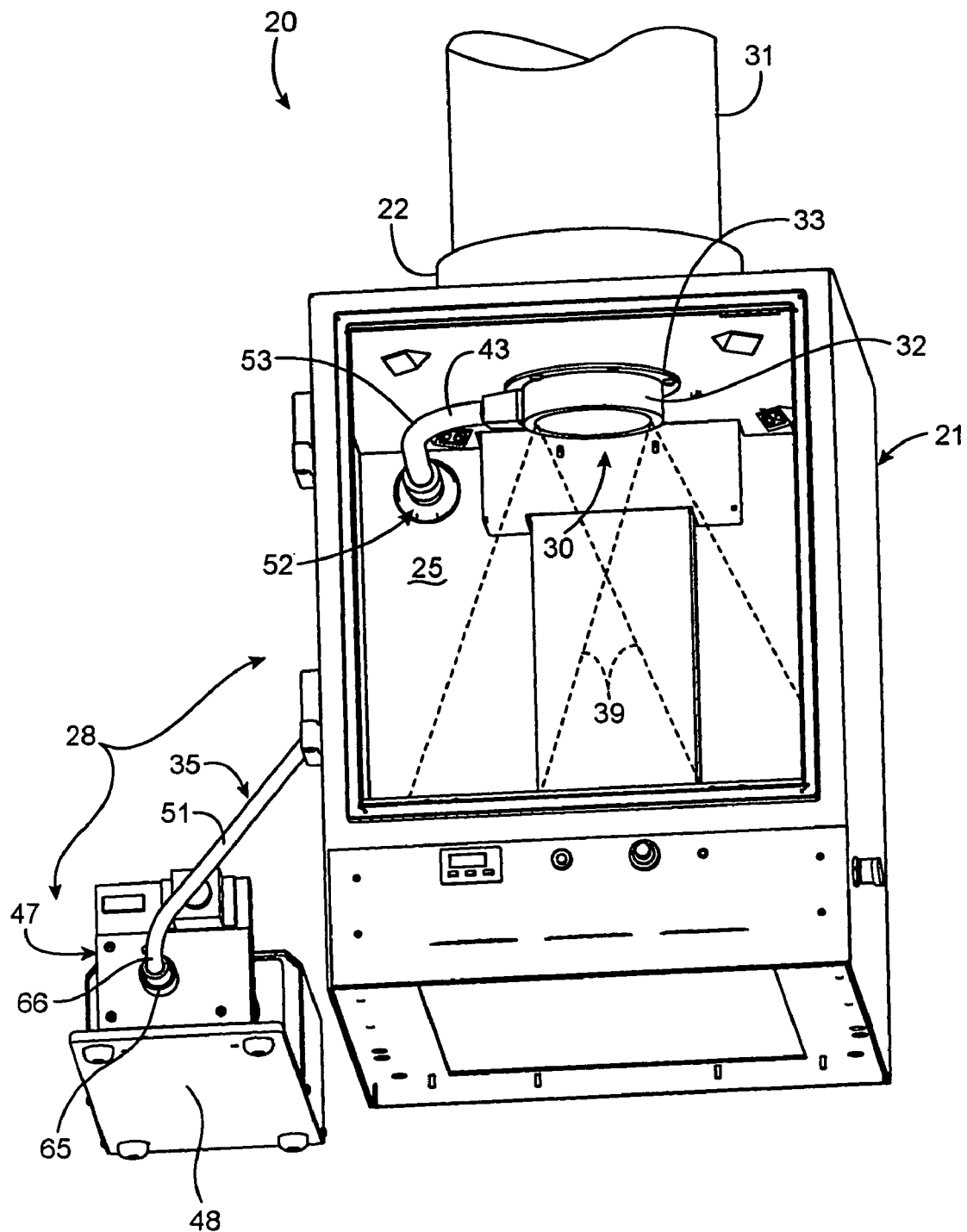
FIG. 2 is a bottom perspective view of the imaging apparatus of FIG. 1, and illustrating a light ring component of the illumination assembly.
Figure 3:
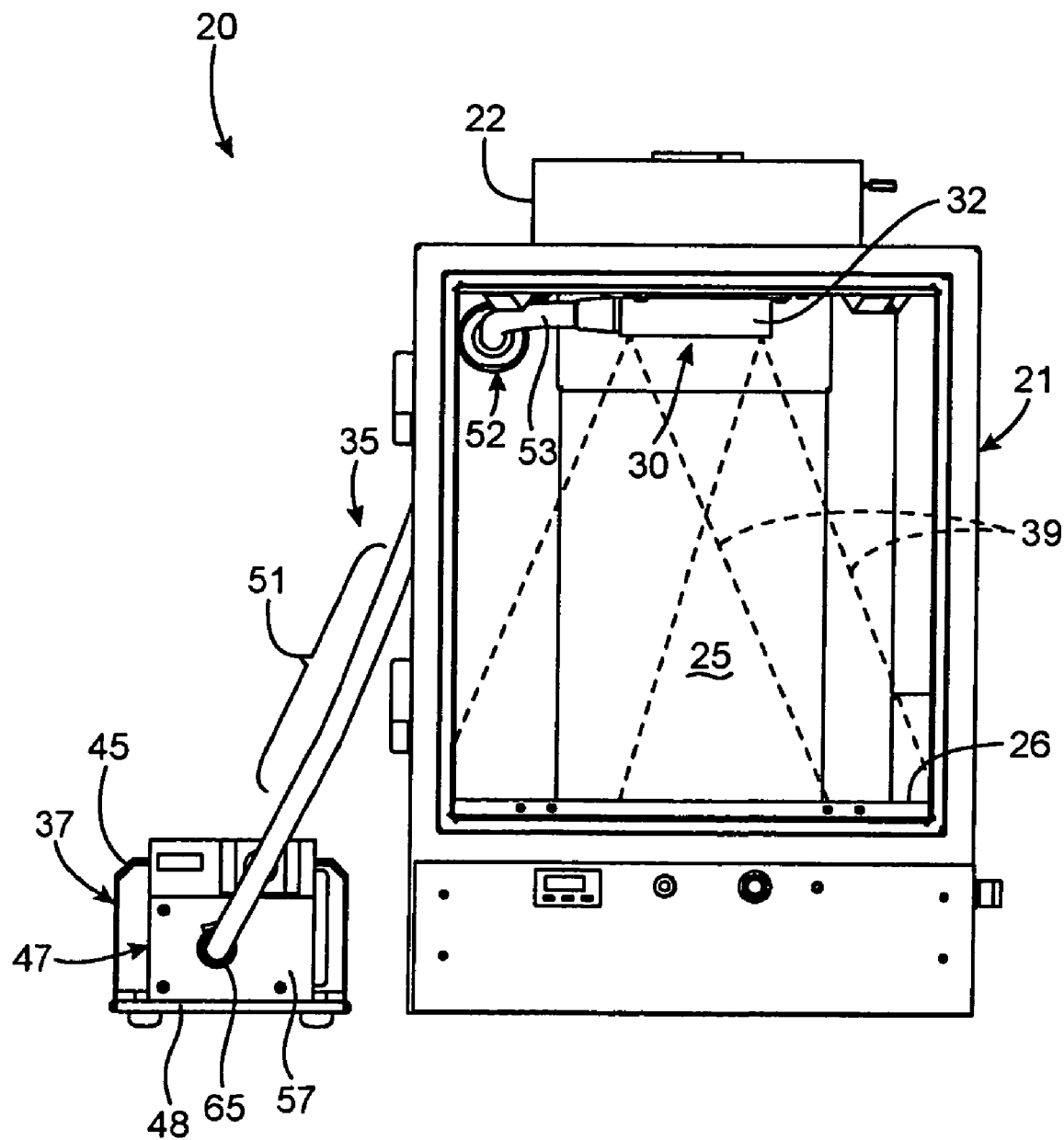
FIG. 3 is a front elevation view of the illumination assembly of FIG. 1 incorporated in the imaging apparatus.
Figure 4:
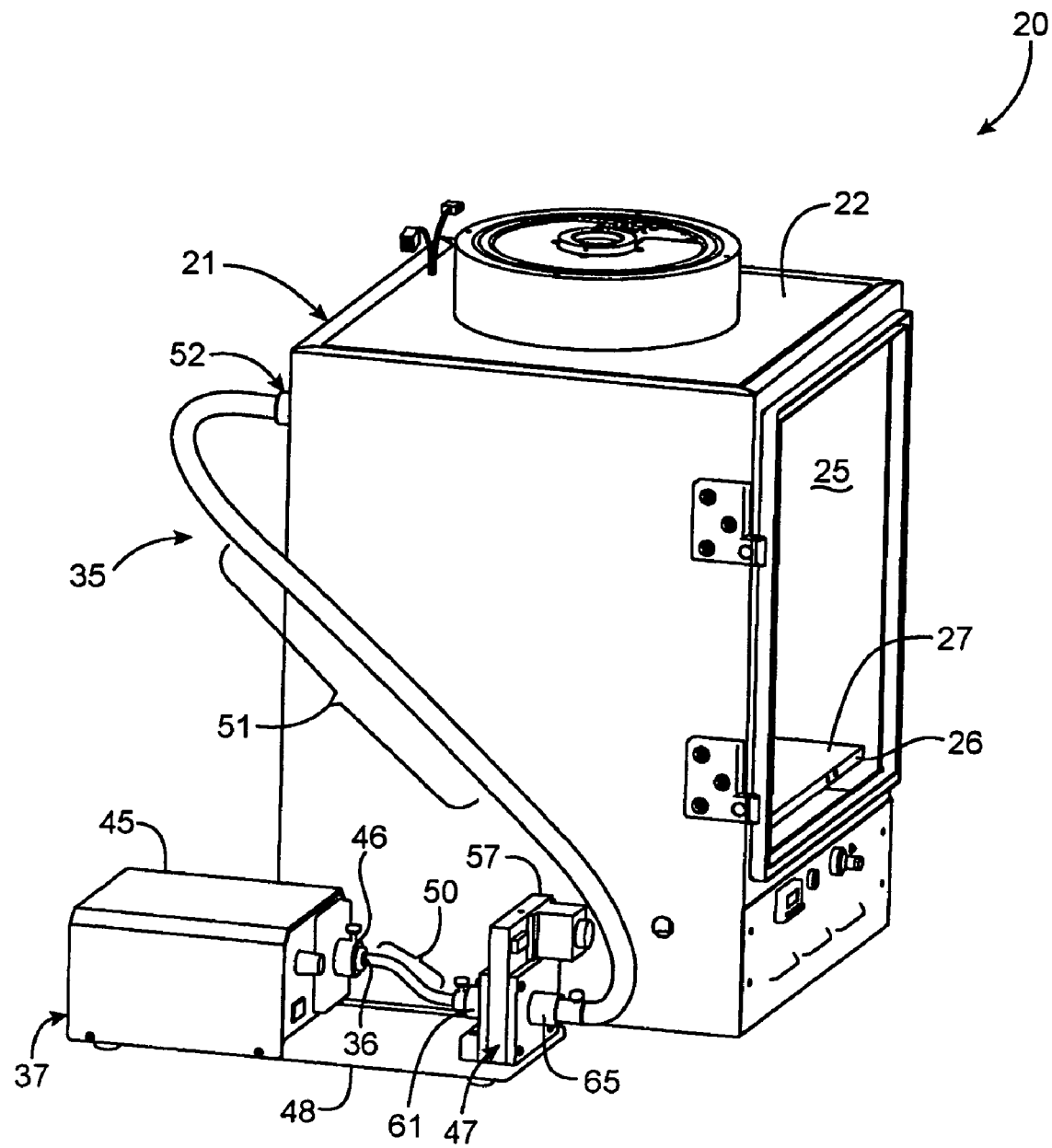
FIG. 4 is a side perspective view of a light source and a filter wheel assembly of the illumination assembly of FIG. 1 optically coupled to the imaging apparatus.
Figure 5:
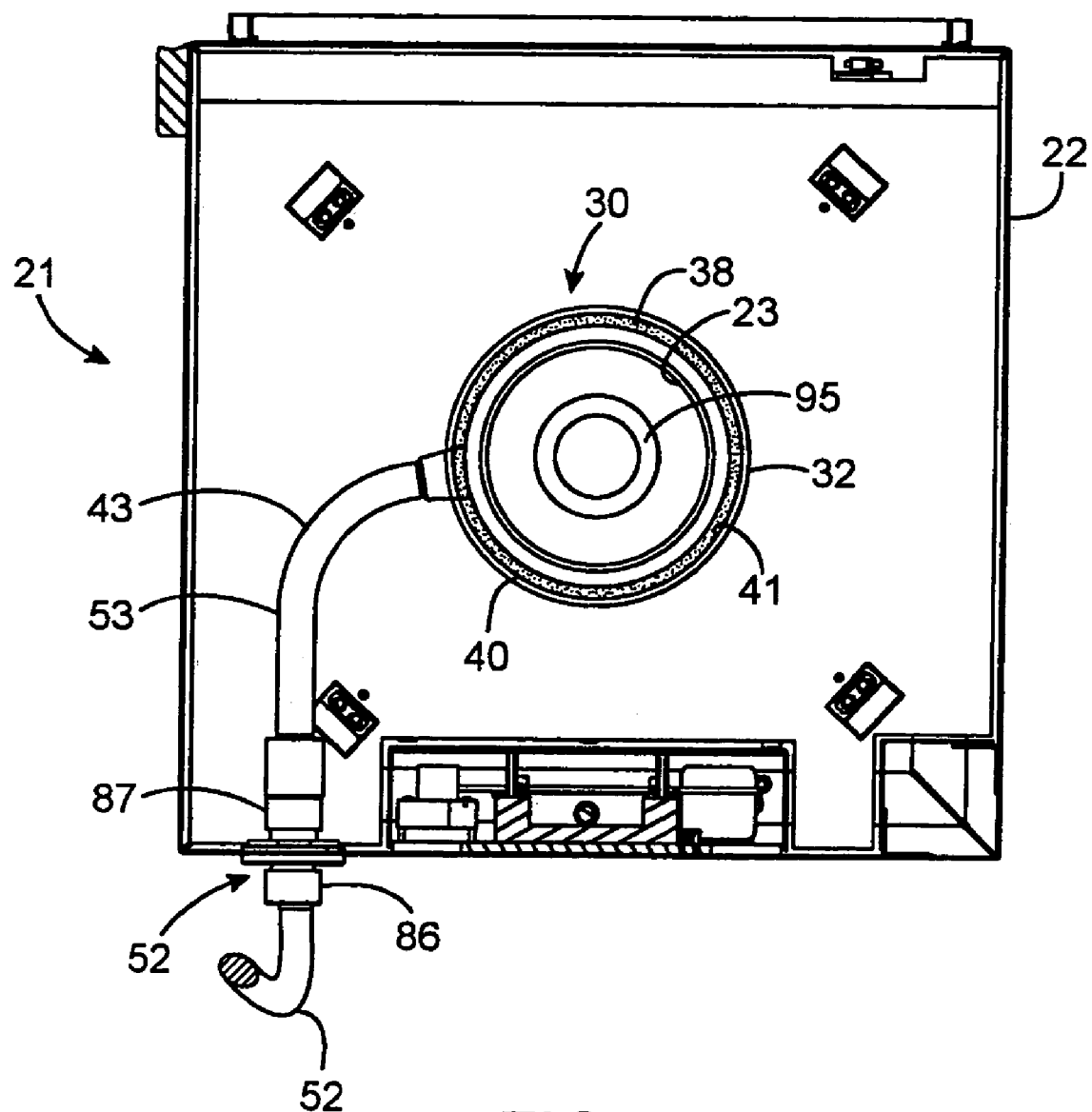
FIG. 5 is an enlarged, bottom plan view of the light ring component of the of the illumination assembly of FIG. 1.

Referring now to FIGS. 2, 4 and 5, the illumination assembly 28 includes a frame 32 supporting the illumination device 30 which is mounted to the upper housing through a nut plate 33. The frame 32 is preferably a rigid, ring-shaped structure having an interior diameter slightly larger than that of the view port 23 (FIG. 5) so as to peripherally surround it without obstructing the view from the lens system. Although the illustrated illumination device and the supporting frame 32 are circular, other geometric forms may be applied as long as the illumination device extends generally around the view port 23.

In one specific embodiment, the illumination device is provided by a fiber optic lighting system having a plurality or bundle 35 of fiber optic strands extending into the imaging compartment 25. The proximal ends 36 of the strands of the bundle 35 are positioned in optical communication with a light source 37 to transmit collected light to the distal ends 38 of the fiber optic strands. To optimize the system for use fluorescent image capture in accordance with the present invention, the material composition of the fiber optic strands are selected to have low auto-fluorescence properties. All materials (glasses, etc.), it will be understood, will fluoresce at some level. Ordinary optical glasses (E.g., float glass, BK7) contain impurities that can fluoresce. Although the autofluorescence of glass is fairly low, the extremely sensitive cameras utilized in the present invention will easily detect the autofluorescence of these materials. The glass (or other material) autofluorescence passes through the emission filter and creates noise in the fluorescence signal, so every effort is made to minimize autofluorescence. One material particularly suitable for the fiber optic strands and filters is high purity fused silica, such as plastic clad fused silica or silica clad fused silica, which has very low autofluorescence.

As shown in FIG. 5, a bottom face 40 of the frame 32 defines an annular slit 41 upon which the distal ends 38 of the strands terminate at a position generally perpendicular to the face 40. Accordingly, the plurality of distal ends 38 of the fiber optic strands each independently emit a conical directional beam of light (illustrated by broken lines 39) onto the specimen platform.

Preferably, a collective cone of light (illustrated by broken lines 39) is emitted having with a full angle of about 55°, wherein each strand emits light in the range of about 50° to about 60°. By positioning the strand distal ends 38 at least about 140 mm to about 380 mm from the specimen platform, the collective ring of conical light beams emitted from strand distal ends 38 sufficiently overlap (FIG. 3) to produce relatively uniform illumination of the specimen. That is, the illumination intensity does not vary by more than about ±25% over the entire field of view, which is between about 10 cm to about 25 cm in these macroscopic applications. Moreover, these diverging beams, as will be discussed below, are substantially directed onto the specimen platform to illuminate only the specimen, and to reduce detrimental florescence of the other box components in the imaging compartment.

The strand distal ends are positioned substantially continuously around the annular slit 41, and are about 3–6 strands wide. It will be appreciated, however, that complete continuity of the strand distal ends is not required to provide uniform lighting in accordance with the present invention. One example of such ring light guides is model 70001148001 by Dolan Jenner Industries of Lawrence, Mass. These fixtures are typically utilized in non-light-tight microscopic applications. Accordingly, these applications are non-fluorescent in nature.

To protect the exterior fiber optic bundle portions 50 and 51 of the fiber optic bundle 35 and to reduce the introduction of exterior light or noise into the fiber optic strands, a segmented, flexible metal jacket (not shown) is placed around these portions which is further surrounded by a flexible PVC sleeve 42. This sleeve is opaque (black), and blocks all external ambient light that might enter the fiber bundle. While this protective sleeve combination is sufficient to substantially reduce the introduction of exterior noise into the fibers (i.e., for use in the exterior bundle portions 50 and 51 outside the of imaging box), it may be phosphorescent and is therefore unsuitable for use inside the box since, in these low-intensity imaging applications, even an amount of light emanating from within the protective sleeve will detrimentally influence the fluorescent imaging of the specimen.

Accordingly, internal to the imaging box, the sleeve material 43 surrounding the bundle portion 53 of the fiber optic bundle 35 is replaced with a non-phosphorescent material to substantially eliminate the possibility of spurious light sources from the fiber optic bundle 35 within the imaging box. One particular flexible material which has low phosphorescence is a polyolefin heat shrink tubing material.

The proximal end 36 of the fiber optic bundle 35 is coupled to a fiber optic light source 37 which optically couples the proximal end faces of the fiber optic strands (not shown) with a direct light of the light source. Preferably, the light source includes a housing 45 which provides a connector 46 to position the proximal end faces of the fiber optic strands substantially adjacent the light source so that the light can be transmitted through the fiber optic strands of the bundle 35. One example of such a Fiber Optic Illuminator is model PL 900, by Dolan Jenner Industries of Lawrence, Mass.

In one embodiment, the direct light is provided by a bulb contained in the housing 45, and positioned at the proximal end faces of the fiber optic strands. A preferred light comprises a tungsten halogen lamp, which emits a wide spectrum of bright white light suitable to fluoresce objects. Other applicable light sources include xenon lamps, mercury lamps and lasers.

Typically, the usable fluorescence spectrum is in the range of 400 nm to about 900nm. Thus, depending upon the desired fluorescence spectra, the composition of the sample material and the fluorescent material, the remaining light emitted by the light source must be filtered out. Optical filters are applied, accordingly, to filter out non-fluorescence spectra as well as unwanted fluorescence spectra. Depending upon the application, there have been selected optical filters or filter wheels disposed in the imaging compartment of an imaging apparatus 21 just after the off-set light source. Such an arrangement, however, would not be practical in the lighting technique of the present invention since the diameter of the ring-shaped frame 32 is significantly larger. Moreover, proportionate to the size of the imaging compartment, a filter wheel could not be deployed.

Figure 6:
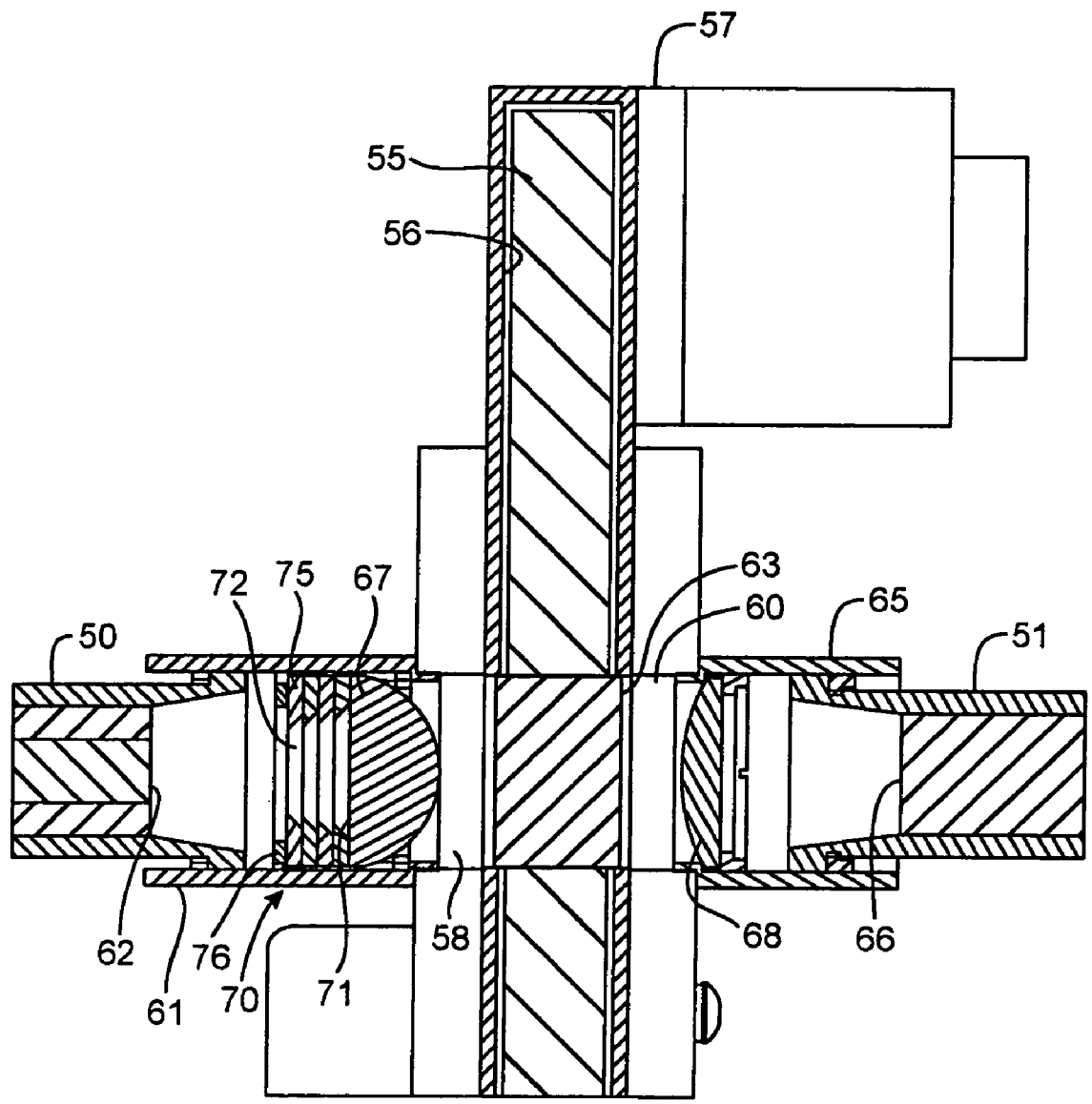
FIG. 6 is an enlarged, side elevation view, in cross-section, of the filter wheel assembly of the illumination assembly of FIG. 1.

In accordance with the present invention, a filter wheel assembly, generally designated 47, is positioned "in-line" in the fiber optic bundle 35 (FIGS. 1, 4 and 6). Preferably, the filter wheel assembly 47, which includes a plurality of optical filters, is positioned in close proximity to the transmission box. This enables the filter wheel assembly and the transmission box to be supported on a common support frame 48, and to be packaged together as a single unit.

Briefly, as best illustrated in FIGS. 2, 4 and 5, the fiber optic bundle 35 includes a first bundle portion 50, extending between the light source 37 and the filter wheel assembly 47, and a second bundle portion 51, extending between the filter wheel assembly 47 and an optical connector assembly 52 mounted to the imaging apparatus 21. Finally, the fiber optic bundle includes a third bundle portion 53 extending from the optical connector assembly 52 (as will be described in greater detail below) on the inside of the imaging compartment 25 to the frame 32. This third bundle portion 53, as above-mentioned, includes the heat shrink material sleeve 43 which has low phosphorescence.

The optical filters are typically interference-type filters which include bandpass filters, longpass filters and shortpass filters. These filters are preferably provided as a filter set contained on a filter wheel 55 of the filter wheel assembly 47 which is placed in-line with the fiber optic bundle 35. Thus, the filter wheel 55, rotatably mounted in a recess 56 of the housing 57, can be selectively rotated to position the selected filter in the path of the fiber optic strands.

Each interference filter is selected to allow the passage of select spectra of light. Another useful parameter, in accordance with the present invention, is selecting a filter with sharp cut-offs or edges so that the gap between the excitation and emission filter bands can be minimized. This is beneficial in that the Stokes shift for many common fluorescent dyes and proteins is relatively small. The Stokes shift is the separation in wavelength between the excitation and emission peak. Usually, a filter gap of about 20 nm is chosen. These filters also are characterized by very high rejection outside the passband or "out-of-band" blocking properties, with a typical rejection of >$10^6$. Furthermore, the filters are also preferably constructed from low auto-fluorescent materials. Accordingly, the application of these higher quality excitation and emission filters allows the use of a single excitation-emission filter pair without an associated dichroic filter.

Examples of such filters include the Alpha Technology filters from Omega Optical, Inc. of Brattleboro, Vt. For a general discussion on fluorescence and filtering, see the *Handbook of Optical Filters for Fluorescence Microscopy*; by Jay Richman of the Chroma Technology Corp, June 2000, and herein incorporated by reference in its entirety. The housing 57 of the filter wheel assembly 47 is substantially light-tight so that detrimental exterior light is not introduced as the light is transmitted through the filters. The housing, as viewed in FIG. 6, further includes an input port 58 and an output port 60 upon which the selected filter optically aligns therewith for the filtering of the light. Accordingly, a first connector 61 is included which is adapted to optically align an optical output end 62 of the first bundle portion 50 within the input port 58 of the housing for transmission of the light through the filter 63. Similarly, the filter wheel assembly 47 includes a second connector 65 which is adapted to optically align an optical input end 66 of the second bundle portion 51 within the output port 60 of the housing for reception of the filtered light from the filter 63.

To facilitate transmission of the light through the filter, a collimating lens 67 is positioned in the input port 58 between the optical output end 62 of the first bundle portion 50 and the filter 63. In order for the excitation filter to function properly, the light rays must be fairly well collimated (parallel to the optical axis) through the filter. Therefore, as the light passes through the collimating lens, it is collimated in a direction substantially perpendicular to the planar face of the filter which minimizes detrimental reflection there from. Further, by selecting the first bundle portion 50 of the fiber optic bundle 35, extending between the light source 37 and the filter wheel assembly 47, to be about ¼ inch in diameter, most of the exiting light rays have a maximum cone angle in the range of about 30° to about 40°. Consequently, after passing through the collimating lens 67, the angle of incidence is reduced to a maximum ray angle of less than or equal to about 12° The output of the excitation filter/lens assembly couples into the ½ inch diameter fiber optic bundle portion 51 in order to mate up with the ring light, which also as a ½ inch bundle size.

A focusing lens 68 is further disposed downstream from the filter 63 to focus and direct the collimated and filtered light, exiting the filter 63, into the optical input end 66 of second bundle portion 51 for transmission through the fiber optic strands thereof. FIG. 6 best illustrates that the focusing lens 68 is positioned in the output port 60 between the filter 63 and the optical input end 66 of the second bundle portion 51 of the fiber optic bundle 35. Typical of these filter wheel assemblies, by way of example, is model FA-448, by Acton Research of Acton, Massachusetts. It will be appreciated, however, that light-tight filter cassettes and filter bars may be employed as well.

While the collective optical arrangement of a conventional filter wheel assembly is applicable for most optical applications, this set-up is not suitable for fluorescent imaging. This is due to the fact that trace amounts of unfiltered light often leak around the periphery of the filter which detrimentally affect the fluorescent imaging of the sample in the imaging compartment. Although the housing 57 of these conventional filter wheel assemblies is considered light-tight, when the angle of transmission of some rays of light exiting the optical output end 62 of the first bundle portion 50 are sufficiently skewed from a direction parallel to the optical axis of the output end, unfiltered light can pass along the outer edges of the collimating lens 67, and thus, past the filter 63 and into the focusing lens.

The skewing of the light rays exiting the collimating lens depends on the distance of the bundle distal end to the collimating lens, as well as the diameter of the bundle and collimating lens, the f-number of the lens and the numerical aperture of the bundle. By way of example, when the diameter of the bundle 62 is in the range of about 6.3mm to 6.4 mm, the diameter of the collimating lens 67 is in the range of about 16.5mm to about 17 mm, the f-number is one and the distance between the optical output end 62 and the collimating lens 67 is in the range of about 19 mm to about 20 mm, a substantially skewed light ray exiting the collimating lens would be one in the range of greater than about 14 degrees from the direction substantially parallel to the longitudinal axis of the perpendicular to the optical output end 62.

In accordance with another aspect of the present invention as is best illustrated in FIG. 6, a light baffle device, generally designated 70, is deployed between the optical output end 62 and the collimating lens 67 to intercept light these skewed light rays. Accordingly, the baffle device 70 will substantially prevent skewed rays from reflecting off of interior walls and entering the collimating lens 67 and thus leak around the filter 63.

The light baffle device 70, in one embodiment, includes an opaque plate member 75 disposed substantially adjacent an upstream abutting surface 71 of the collimating lens. Centrally disposed in the plate member is an aperture 72 extending there through, and having a transverse cross-sectional area smaller than that of the collimating lens abutting surface 71. Preferably, the ratio of the transverse cross-sectional area of the aperture 72 to that of the abutting surface 71 of the collimating lens 67 is in the range of about 0.64:1 to about 0.8:1.

Thus, the skewed light rays impinging upon the upstream surface 73 of the plate member 75 are intercepted, while the remaining portion of the light transmitted from the first bundle portion 50 pass through aperture 72. Further, to reduce reflection of these impinging light rays, the plate member 75 is either coated with a material which absorbs light, such as black anodize, or is composed of opaque materials having absorption properties, such as black Delrin.

In the preferred form, the aperture 72 of the baffle device 70 is substantially central to the abutting surface 71 of the collimating lens 67. Thus, a longitudinal axis of the aperture 72 is substantially co-axially aligned with a longitudinal axis of the collimating lens 67.

In still another configuration, a plurality of plate members $75_A$–$75_D$ are nested together in a side-by-side manner in abutment with the collimating lens abutting surface. Briefly, while four plate members $75_A$–$75_D$ are shown and described, it will be appreciated that more or less plate members may be applied.

Figure 7:
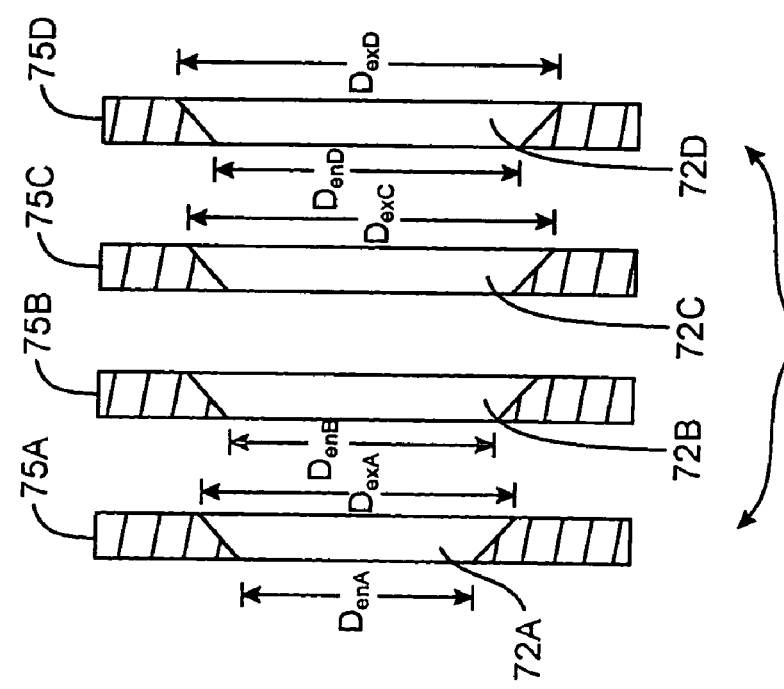
FIG. 7 is an enlarged, exploded, side elevation view, in cross-section, of the plate members of a baffle device of the filter wheel assembly of FIG. 6.
Figure 8:
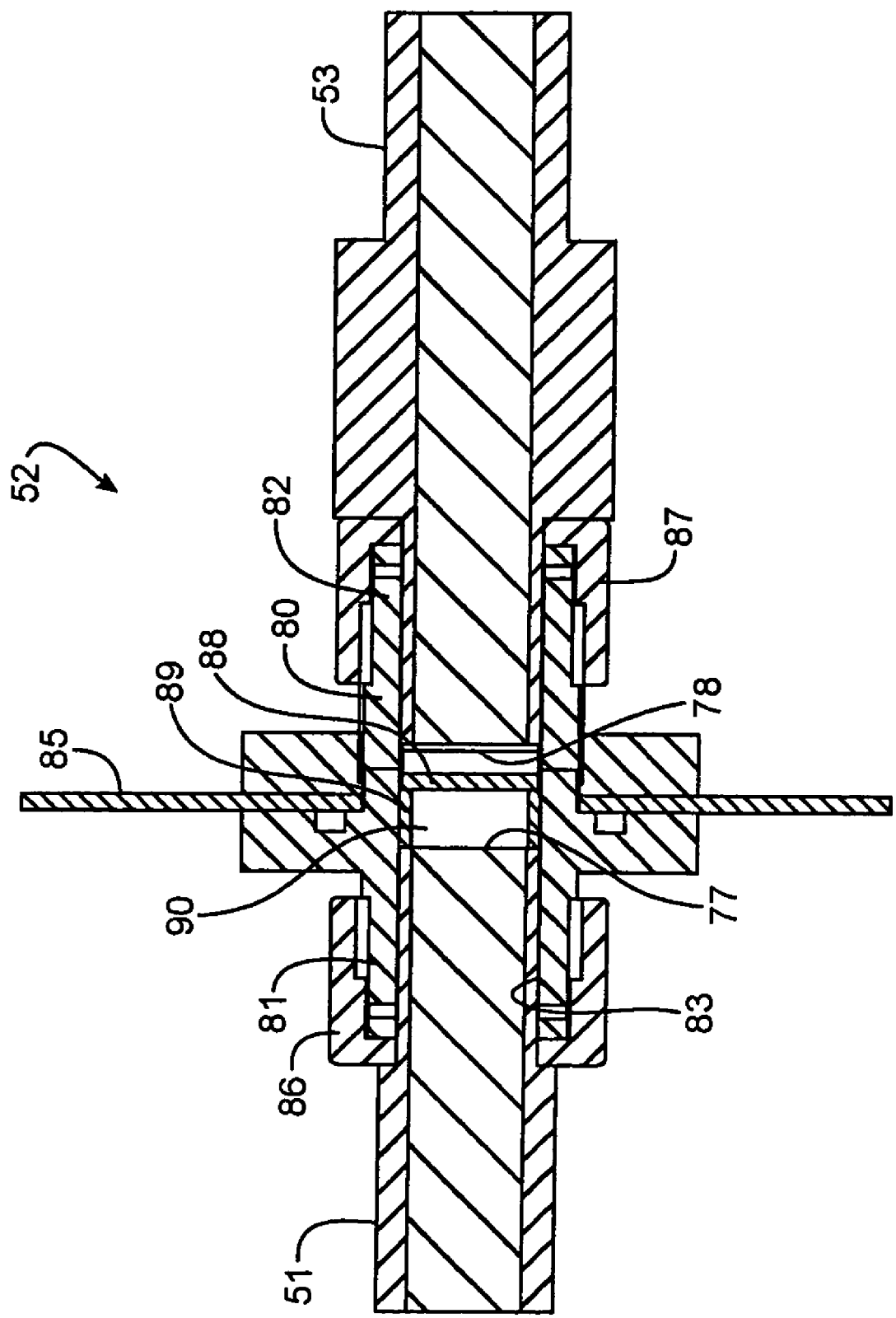
FIG. 8 is an enlarged, fragmentary side elevation view, in cross-section, of an optical connection assembly of the illumination assembly of FIG. 1.

FIGS. 6 and 7 further illustrates that each plate member $75_A$–$75_D$ defines a respective central aperture $72_A$–$72_D$ which is co-axially aligned with the longitudinal axis of the abutting surface 71 of the collimating lens. A threaded ring 76 or the like is deployed in the input port 58 and matably engaged with the first connector 61 to affix the plate member $75_A$–$75_D$ against the abutting surface 71 of the collimating lens 67. Further, each aperture $72_A$–$72_D$ has a respective transverse cross-sectional area smaller than that of the collimating lens abutting surface 71. However, each adjacent downstream plate member $75_B$–$75_D$ defines a respective aperture $72_B$–$72_D$ having a diameter incrementally larger than its adjacent upstream plate member $75_A$–$75_C$. Preferably, the area of each successive downstream aperture $72_B$–$72_D$ is about 10% to about 25% larger.

Each aperture $72_A$–$72_D$ further tapers outwardly in a direction toward the collimating lens 67 such that a respective entrance diameter ($D_{en}$) of the respective aperture $72_A$–$72_D$ is smaller than the corresponding exit diameter ($D_{ex}$) thereof. Preferably, the outward taper of each aperture is in the range of about 30° to about 60° from the longitudinal axis, and the thickness of each plate member is in the range of about 0.5 mm to about 2.0 mm.

However, in accordance with the present invention, while the overall transverse cross-sectional dimension of each successive downstream aperture $72_B$–$72_D$ is progressively larger, the entrance Diameter ($D_{en}$) of the corresponding downstream aperture $72_B$–$72_D$ of the plate member $75_B$–$75_D$ is smaller than the exit Diameter ($D_{ex}$) of the adjacent aperture $72_A$–$72_C$ of the adjacent upstream plate member $75_A$–$75_C$. Accordingly, if this nested configuration of the plate members were provided as an integral single unit, a plurality of annular ribs and adjacent troughs would be defined with each annular rib being successively larger in diameter as the plate member is positioned closer to the collimating lens 67.

This is beneficial in that should a sufficiently skewed light ray pass through the upstream aperture 72, it may be intercepted in the annular trough between two adjacent ridges.

In another aspect of the present invention, a light-tight fiber optic connection assembly, generally designated 52, is included for optically connecting the distal transmission end 77 of second bundle portion 51 to the proximal receiving end 78 of third bundle portion 53. This optical connector assembly 52, as best viewed in FIGS. 2, 4, 8 and 9, includes a connector body 80 mounted to a side wall 85 of the imaging apparatus 21 for optical communication into the light-tight imaging compartment 25.

The connector body 80 includes a proximal portion 81 and an opposite distal portion 82, and defines an elongated passage 83 extending from the proximal portion 81 to the distal portion 82. The proximal portion 81 of the connector body is adapted to removably couple to a distal optical connector 86 mounted to the second bundle portion 51, while the distal portion 82 of the connector body is adapted to removably couple to a proximal optical connector 87 mounted to the third bundle portion 53. Each of the distal optical connector 86 and the proximal optical connector are conventional female optical connectors which are threaded to the corresponding threaded male end of the connector body.

When the optical connectors 86, 87 are properly mounted to the connector body 80, the transmission ends 77 of the fiber optic strands of the second bundle portion 51 terminate in the passage 83 in opposed relationship to the receiving ends 78 of the fiber optic strands of the third bundle portion 53. A diffuser device 88 is further disposed in the passage 83 in the gap region 90 between the second bundle transmission end 77 and the third bundle receiving end 78. This diffuser device 88 is adapted to diffuse the light transmitted from the transmission end of the fiber optic strands to facilitate receipt in the receiving end.

As the collective light is diffused while passing through diffuser device 88, it is substantially uniformly distributed about the proximal receiving ends 78 of the third bundle portion 53. Consequently, the light ring mounted peripherally about the view port 23 uniformly illuminates the specimen platform 26. Without this diffuser, the collimated and filtered light transmitted across the gap may develop "hotspots" on the proximal receiving end 78 of the third bundle portion 53 which causes distribution non-uniformity from the light ring.

The diffuser may be any substantially transparent device capable of uniform diffusion of the light passing there through. Preferably, the diffuser device 88 is composed of a rigid material, such as plastic or glass which is seated across the transverse cross-sectional dimension of the connector body passage 83. To provide uniform light diffusion, at least one surface of the diffuser device 88 upon which the light must pass through is frosted. Typical of these diffusers, by way of example, is model L45-652, by Edmund Scientific of Barrington, N.J.

Figure 9:
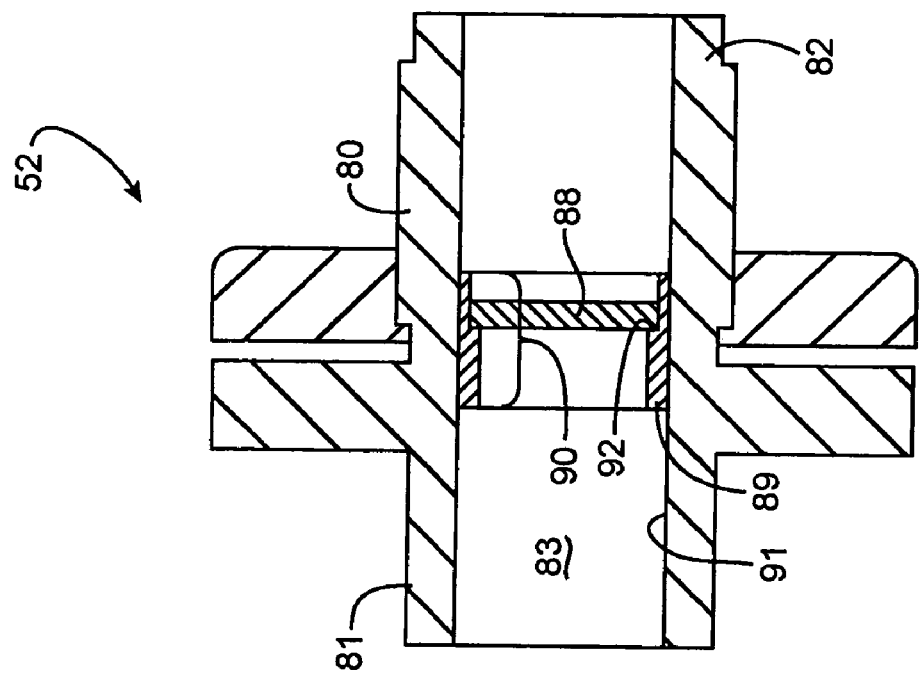
FIG. 9 is an enlarged, side elevation view, in cross-section, of the optical connection assembly of FIG. 8.

As illustrated in FIG. 9, the diffuser device 88 is preferably plate-like having substantially flat, opposed surfaces, of which at least one is frosted. Preferably, an interior wall 91 of the connector body, defining the passage 83, is substantially cylindrical-shaped. An insert sleeve 89 having an outer diameter substantially similar to but smaller than that of the passage 83 is slideably inserted between the transmission ends 77 and the receiving ends 78 of the strands in the gap region 90. The insert sleeve 89 includes an annular shoulder portion 92 upon which the outer circumferential edge of diffuser device 88 seats. When the insert sleeve 89 is slideably disposed in the gap region 90 of the passage 83, the opposed surfaces of the diffuser device 88 extend across the entire transverse cross-sectional dimension of the passage 83 to assure the light transmitted from the distal end of the second bundle portion 51 of the fiber optic strand bundle passes through the diffuser device. By way of example, for a fiber optic bundle with a diameter of about 12.6 mm to about 12.7 mm, the connector body passage 83 may have a diameter in the range of about 12.7 mm to about 12.8 mm. Upon mating of the optical connectors to the connector body, the gap between the opposed ends of the second bundle portion 51 and the third bundle portion 53 may be in the range of about 8.0 mm to about 15.0 mm. The diffuser device 88 accordingly, may have a thickness in the range of about 1.0 mm to about 2.2 mm.

Figure 10:
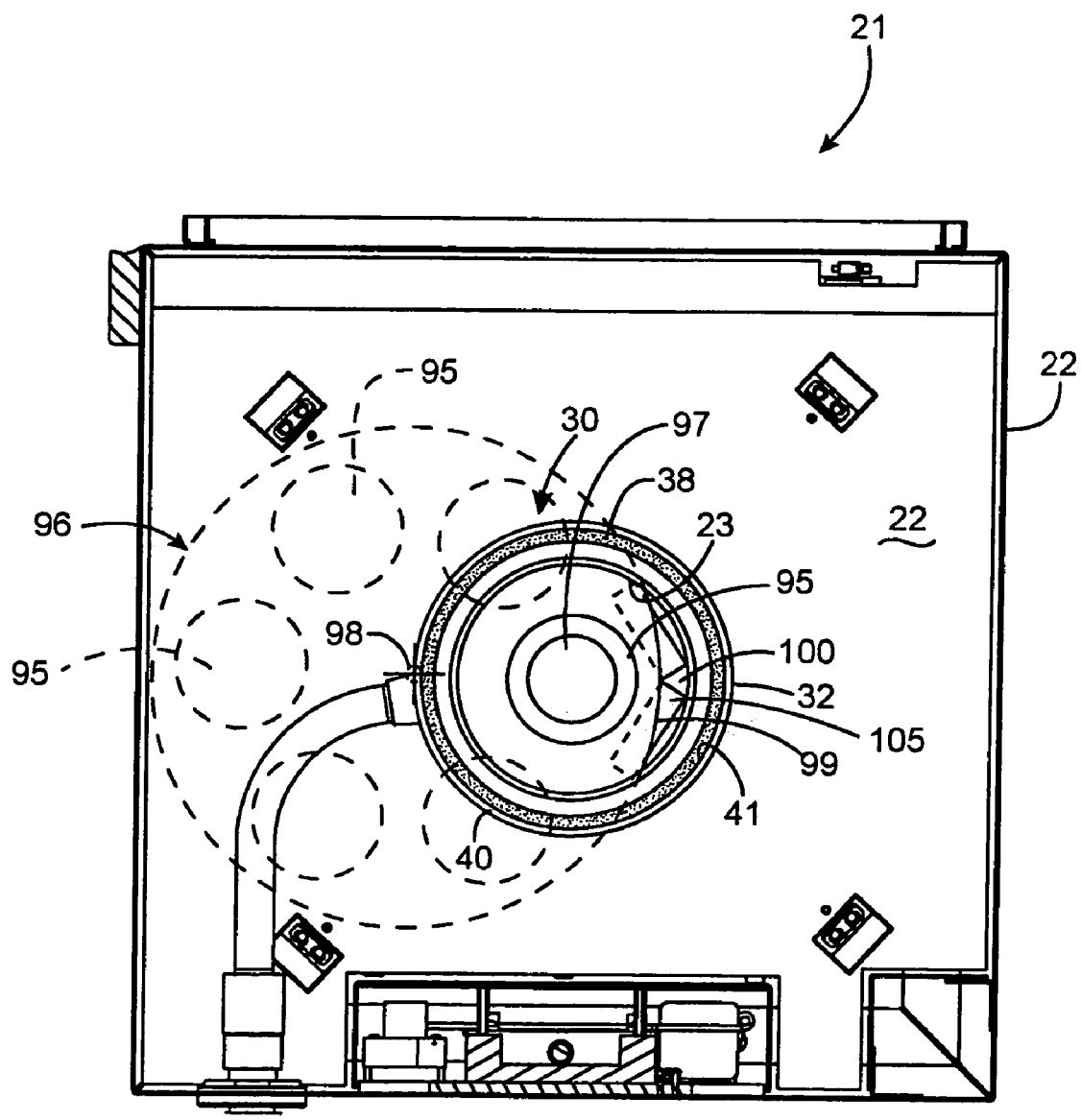
FIG. 10 is an enlarged, bottom plan view of the light ring component of the of the illumination assembly of FIG. 1, and illustrating a second light filter thereof in phantom lines.
Figure 11:
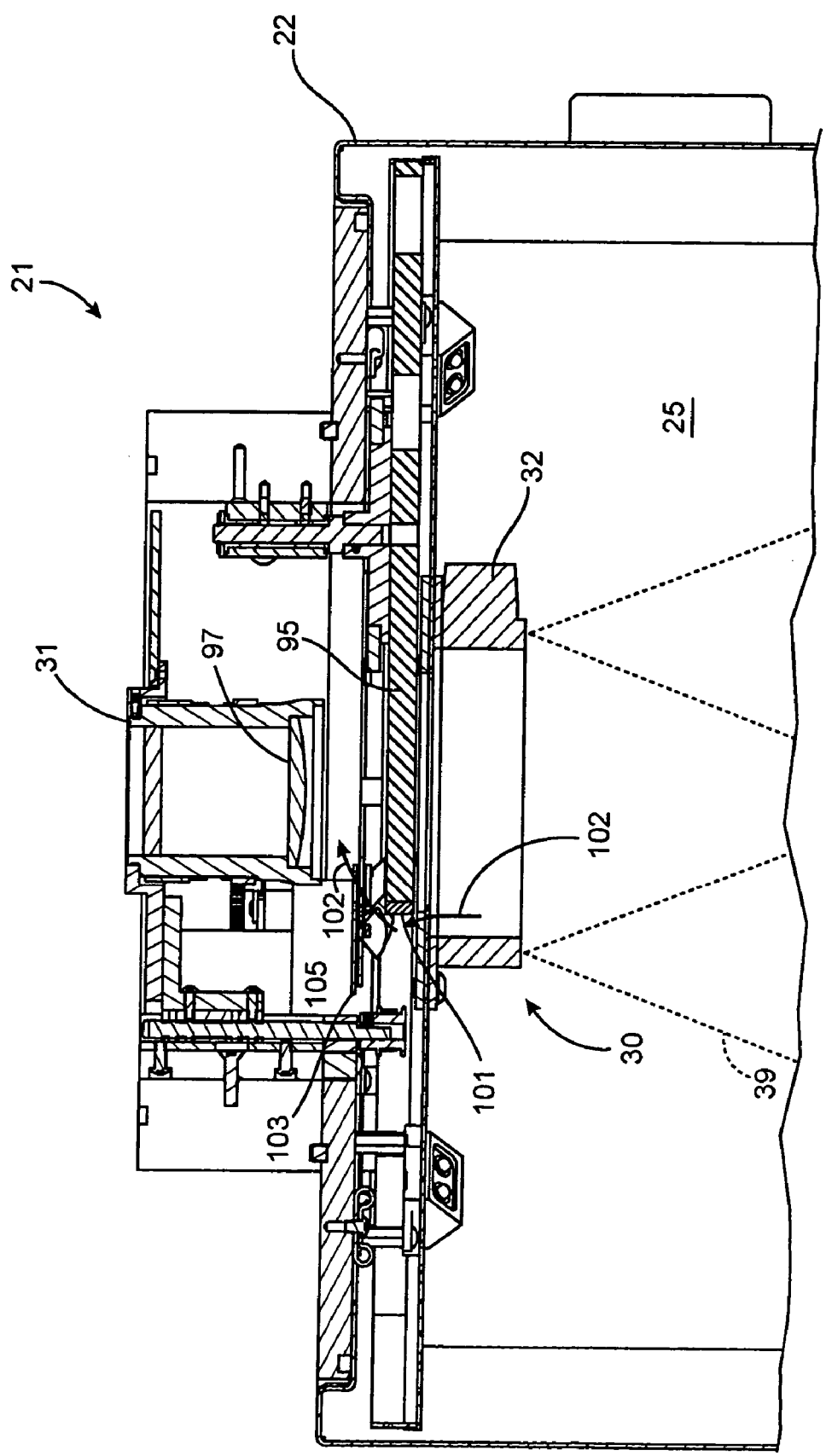
FIG. 11 is a side elevation view, in cross-section, of the light-tight seal mechanism and second filter wheel taken substantially along the plane of the line 11—11 in FIG. 10.

Referring now to FIGS. 10 and 11, an emission filter wheel 96 is housed in the imaging chamber 25 to filter out the excitation light rays, leaving substantially only the fluorescent rays emanating from the sample for capture by the CCD camera 31. Depending upon which excitation filter is necessary in the excitation filter wheel 57 to excite the desired fluorescent spectra in the imaging compartment 25, a corresponding emission filter 95 is selected to absorb the excitation rays and allow passage of the fluorescent emission into the lens 97 of the camera 31.

In one specific embodiment, emission filter wheel 96 is rotatably mounted to the upper housing 22 of the imaging apparatus 21, between the frame 32 of the light ring 30 and lens 97 of the camera 31 (FIG. 11). As best viewed in FIG. 10, the filter wheel includes a plurality of filters each of which can be selectively rotated about optical filter wheel axis 98, and into optical alignment with the aperture of the light ring 30.

Due to size constraints and limitations, a crescent-shaped gap 100 may be formed between the outer peripheral edge 101 of the frame 99 of the filter wheel 96 and the view port 23 of the upper housing 22 (FIG. 10). While this gap 100 is not large, it is sufficient to permit the passage of some unfiltered light rays along the path of arrow 102 in FIG. 11. Accordingly, to prevent this light leakage, a light-tight seal device 105 is positioned between the filter wheel frame 99 and the upper wall 103 of the upper housing.

This seal device 105 is sufficiently dense and/or opaque to prevent the passage of light there through yet sufficiently flexible to allow relative rotation of the second filter wheel without exerting undue stress thereon. Preferably, the seal device 105 is provided by a pair of brush devices positioned in the gap. One such brush material is a plastic brush, by Amesbury Group, Inc. of Statesville, N.C.

Referring now to FIGS. 12–14, 18 and 19, another specific embodiment of the macroscopic fluorescence illumination assembly 28 is illustrated. In this configuration, the illumination assembly 28 includes a fluorescent light source 37, and a light dispersion assembly 110 positioned proximate the view port 23 of the interior wall 103. The illumination assembly 28 further includes a bundle 111 of fiber optic strands composed of substantially pure fused silica. The proximal ends 112 thereof in optical communication with the light source 37 and distal ends 113 thereof terminate proximate the view port 23. The distal ends 113 each emit a conical directional beam of light originating from the light source 37 and cooperating with the light dispersion assembly 110 such that the plurality of directional beams 115 (shown in phantom lines) collectively illuminate the specimen platform 26 in a substantially uniform manner.

As mentioned above, all materials (glasses, etc.) fluoresce at some level. Ordinary optical glass materials applied for fiber optic strands contain impurities that can fluoresce. It has been observed that high purity or substantially pure fused silica exhibits very low autofluorescence. This is of course beneficial to reduce undesirable autofluorescence of the fiber optic strand material which passes through the emission filter and may be mistaken for "sample" fluorescence. In particular, the fiber optic strands and filters are composed of as plastic clad fused silica or silica clad fused silica.

High purity or substantially pure fused silica is less flexible than glass or other conventional materials applied for fiber optic strands. Thus, the permissible bending radius or radius of curvature of a bundle of fiber optic strands (i.e., the minimum suggested usable bending radius of the fiber optic bundle without fracture of the strands) composed of such fused silica is substantially greater than that for conventional fiber optic strand materials. A fused silica core/clad diameter must be significantly reduced to obtain the same radius of curvature. Thus, about twice as many fused silica fibers must be used to transmit the same amount of light, and the cost becomes a significant factor.

Figure 12:
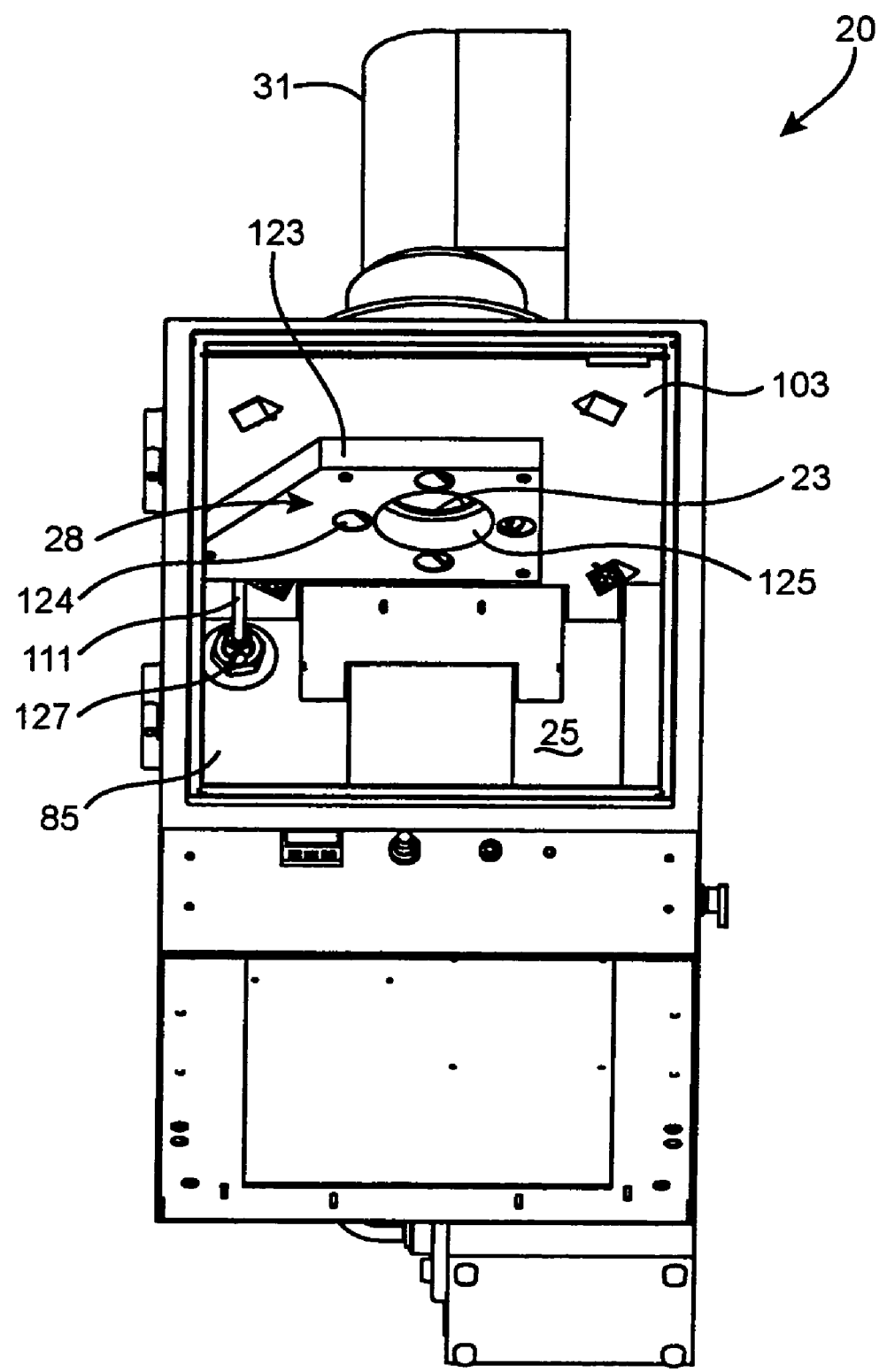
FIG. 12 is an enlarged, bottom perspective view of the imaging apparatus of FIG. 1, and illustrating an alternative embodiment illumination assembly.
Figure 13:
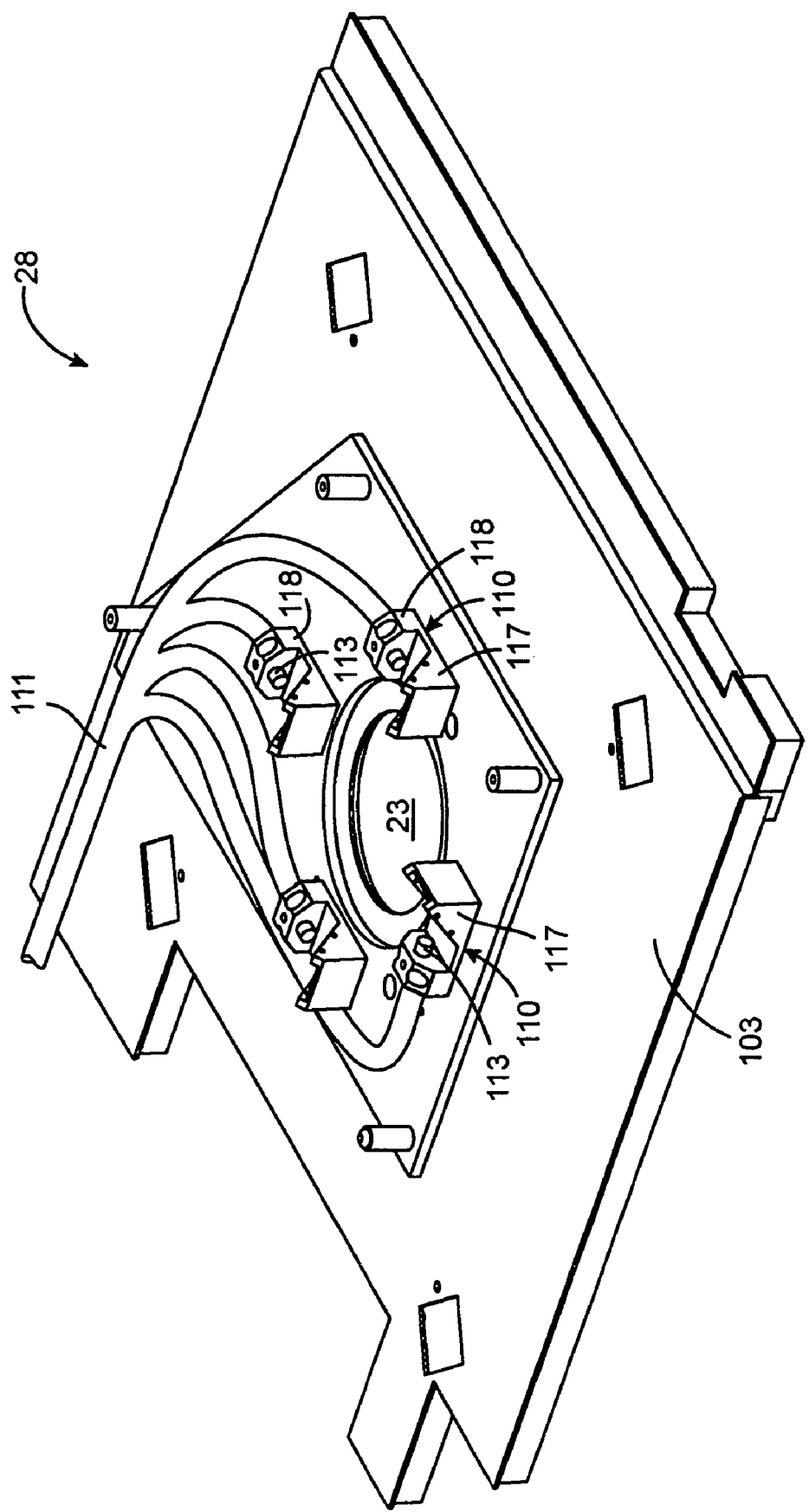
FIG. 13 is an enlarged, bottom perspective view of the alternative embodiment illumination assembly of FIG. 12 mounted to the upper interior wall of the imaging apparatus.
Figure 14:
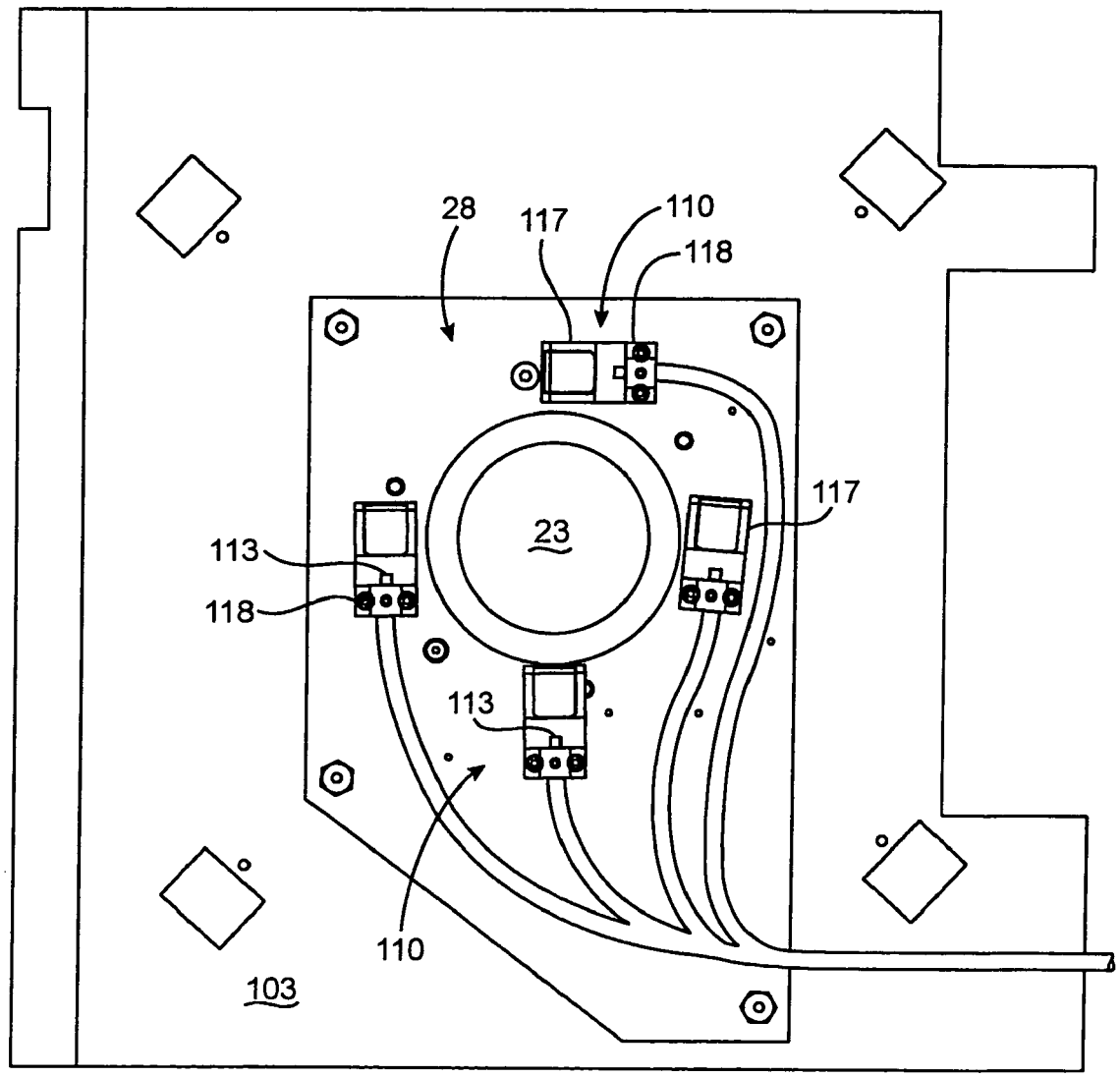
FIG. 14 is a bottom plan view of the alternative embodiment illumination assembly of FIG. 12.

In this specific embodiment, since the bundle of fiber optic strands originates from an interior side wall 85 of the imaging apparatus 21, as shown in FIG. 12, similar to the light-ring embodiment above, the optical axes of the bundle are contained in a generally horizontal plane which is generally parallel with that of the specimen platform 26. Thus, the optical axis of the distal ends of the strands needs to be redirected and repositioned in a direction toward the specimen platform of illumination thereof. However, due to the relatively large radius of curvature of the substantially pure fused silica strands, the overall vertical footprint of the imaging apparatus and costs are significantly increased.

To address this problem, the dispersion assembly 110 is configured to cooperate with the distal ends 113 of the fiber optic strands to redirect the directional beams 115 (shown in phantom lines) collectively toward the specimen platform 26 for illumination thereof in a substantially uniform manner. Accordingly, the optical axes of the distal ends 113 of the fiber optic strands may be retained generally parallel to the specimen platform 26, while the directional beams are directed (E.g., through reflective surfaces 116) downwardly toward the specimen platform 26. The overall height of the imaging apparatus 21, thus, is significantly reduced since the distal ends of the substantially pure fused silica fibers themselves need not be curved toward the platform 26, and the overall cost is significantly reduced.

Figure 15:
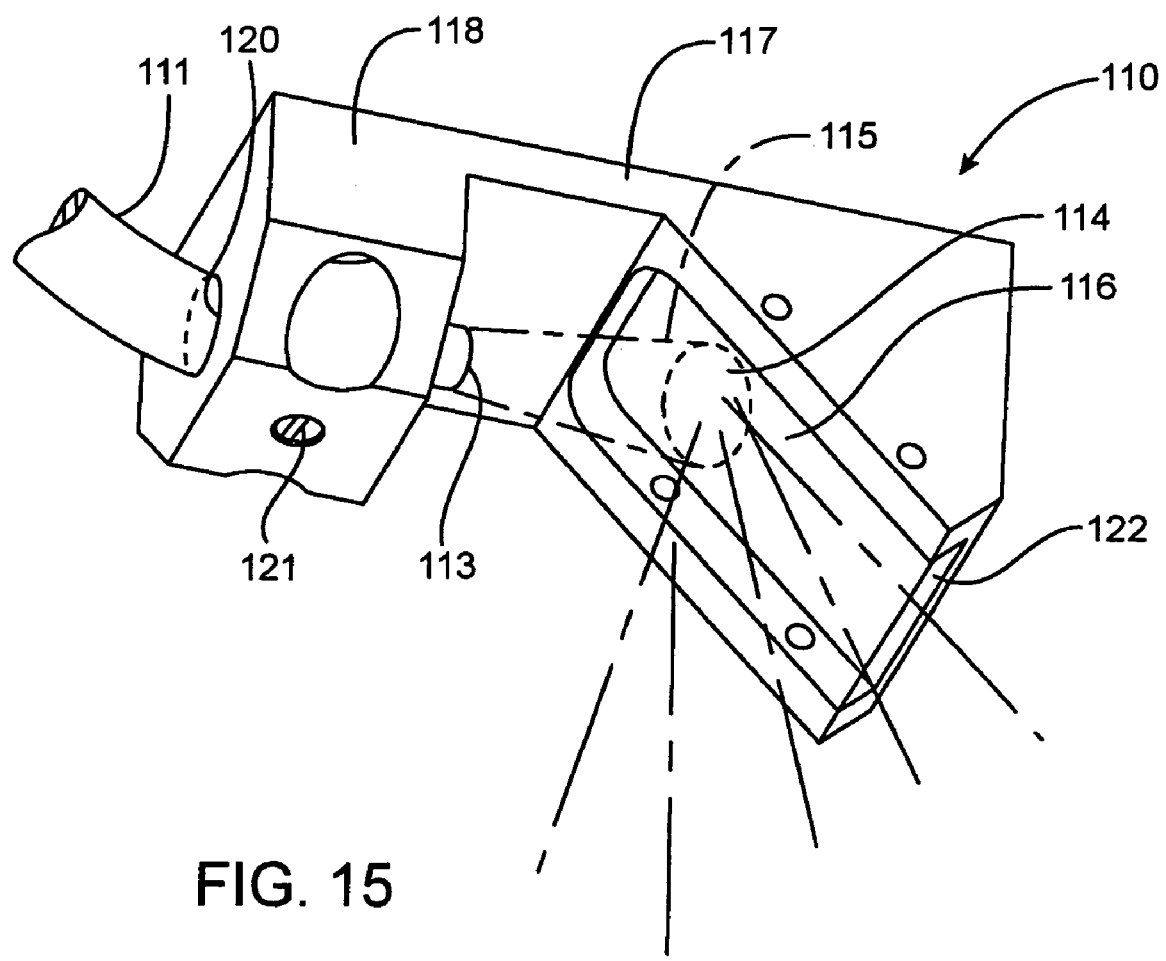
FIG. 15 is an enlarged, bottom perspective view of a light dispersion assembly of the illumination assembly of FIG. 12.
Figure 16:
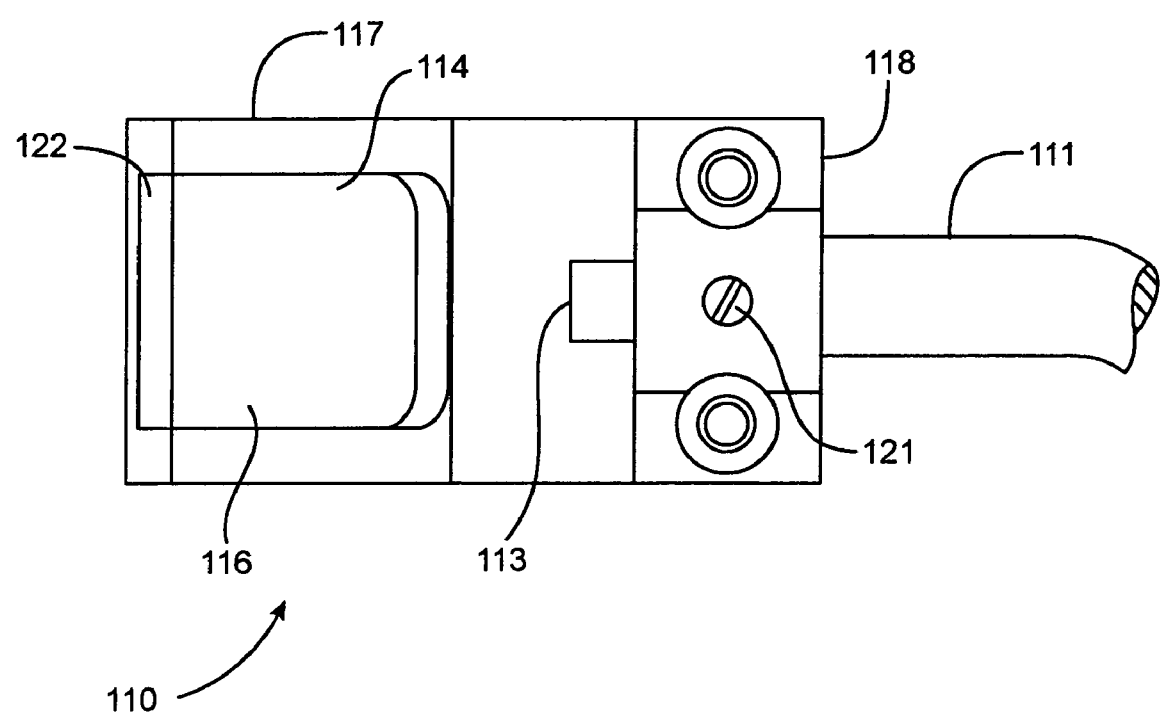
FIG. 16 is an enlarged, bottom perspective view of the of the light dispersion assembly of FIG. 12.

Referring now to FIGS. 15 and 16, the light dispersion assembly 110 includes a bracket device 117 adapted to mount and secure the distal ends 113 of the fiber optic strands to the upper interior wall 103 of the imaging apparatus 21. These bracket devices 117 are preferably substantially rigid, and are composed of black anodized aluminum to reduce auto fluorescence.

In one specific embodiment, to redirect the directional beams emitted from each distal end 113 of the strands, the dispersion assembly 110 includes a reflective surface 116 angled to reflect the directional beams toward the specimen platform 26. This permits the entire fiber optic bundle 111 to be maintained in generally the same plane which is essentially parallel to the specimen platform 26.

To reflect the directional beams about 90° from the optical axis of the distal ends of the strands and toward the specimen platform, the relatively planar reflective surface 116 should be oriented about 45° relative the direction of the optical axis. It will be appreciated that depending upon the particular position of the bracket device 117 and the exact orientation of the optical axis from the relative the desired position along the specimen platform to be illuminated, the angle of the reflective surface can be altered accordingly.

In one application, illumination "hot spots" can be reduced by diffusing the directional beams as they reflect off of the reflective surface 116. This improves the light distribution across the specimen platform so that the illumination is substantially uniform. One diffuser technique is to provide a diffusing surface 114 which cooperates with the reflective surface 116 to uniformly diffuse the directional beams emitted from the strand distal ends 113. For example, the reflective surface 116 may be provided by an aluminum plate with a roughened surface or by SPECRALON®, which diffuses the reflected light as it impinges the surface thereof.

Another diffuser technique is to provide slightly convex reflective surface configured to provide substantially uniform illumination across the specimen platform 26. Other conventional diffuser techniques or a combination thereof may be employed without departing from the true nature and scope of the present invention. Moreover, the desired diffusion pattern after reflection off of the reflective surface is dependent in-part on the particular shape and radius of the convex reflective surface, the distance of the surface from the reflective surface, and the distance from the reflective surface to the specimen platform.

Each bracket device 117 includes a mounting section 118 adapted to removably secure the distal ends 113 of the fiber optic bundle in a manner directing their emitted directional beams of light against the reflective surface 116. As best viewed in FIGS. 15 and 16, the mounting section defines a passage 120 which is formed and dimensioned for sliding receipt of the fiber optic bundle 111 there through. An adjustable fastener 121 affixes the bundle to the bracket device to enable the distal ends 113 of the fiber optic strands to be displaced closer to or further away from the reflective surface 116 during calibration. In one example, the fastener may be simply be a set screw or the like.

FIG. 16 best illustrates that the distal ends 113 of the strands are positioned relatively close to the reflective surface 116 of the mirror, without actual contact therewith. By positioning the distal ends relatively close to the reflective surface, the diffusion of the reflected directional beams are better controlled to be substantially within the specimen platform 26 boundaries. However, it should be appreciated that the distal ends should not be too close or in contact with the reflective surface so as to minimize reflection back through the strand distal ends 113.

For example, the distal ends of the fiber optic strands, in one specific configuration, are positioned in the range of about 6 mm to about 11 mm from the reflective surface, and more preferably about 8 mm. In this example, the reflective surface 116 of the reflector 122 is positioned in the range of about 120 mm to about 460 mm from the specimen platform. Thus, the collective vertical footprint of this configuration is significantly reduced by applying this dispersion assembly.

Preferably, the dispersion assembly includes a plurality of bracket devices 117 peripherally spaced about the view port 23 of the interior wall 103. Such peripheral spacing even more uniformly distributes the reflected directional beams about the view port 23, and further reduces shadowing. Four (4) to eight (8) bracket devices 117 have been found sufficient to assure illumination uniformity, but more or less may be applied as well.

Figure 17:
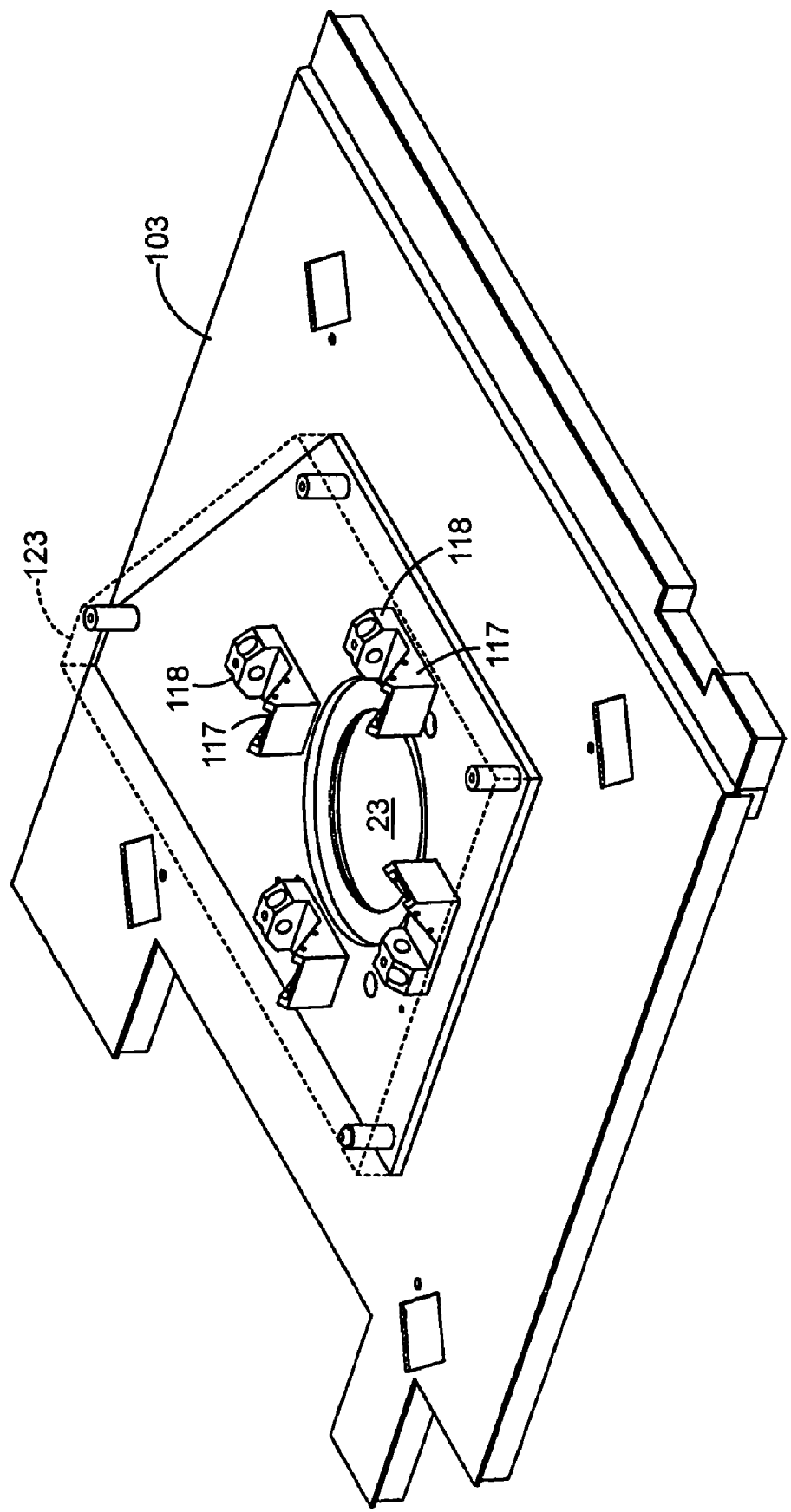
FIG. 17 is an enlarged, bottom perspective view of the alternative embodiment illumination assembly of FIG. 12 illustrating the protective cover device shown in phantom lines.

Referring now to FIGS. 12 and 17, the illumination assembly 28 may include a protective cover device 123 (shown in phantom lines in FIG. 17). This cover provides protection for the lighting components as well as reduce the residual auto fluorescence of the lighting components. The protective cover device 123 includes corresponding apertures 124 (FIG. 12) each aligned with the respective reflective surface 116, and extending through the bottom wall of the cover device to permit passage of the reflected directional beams. Further, a larger aperture 125 corresponding to and aligned with the view port 23 is provided to enable passage of the light to the camera.

Figure 18:
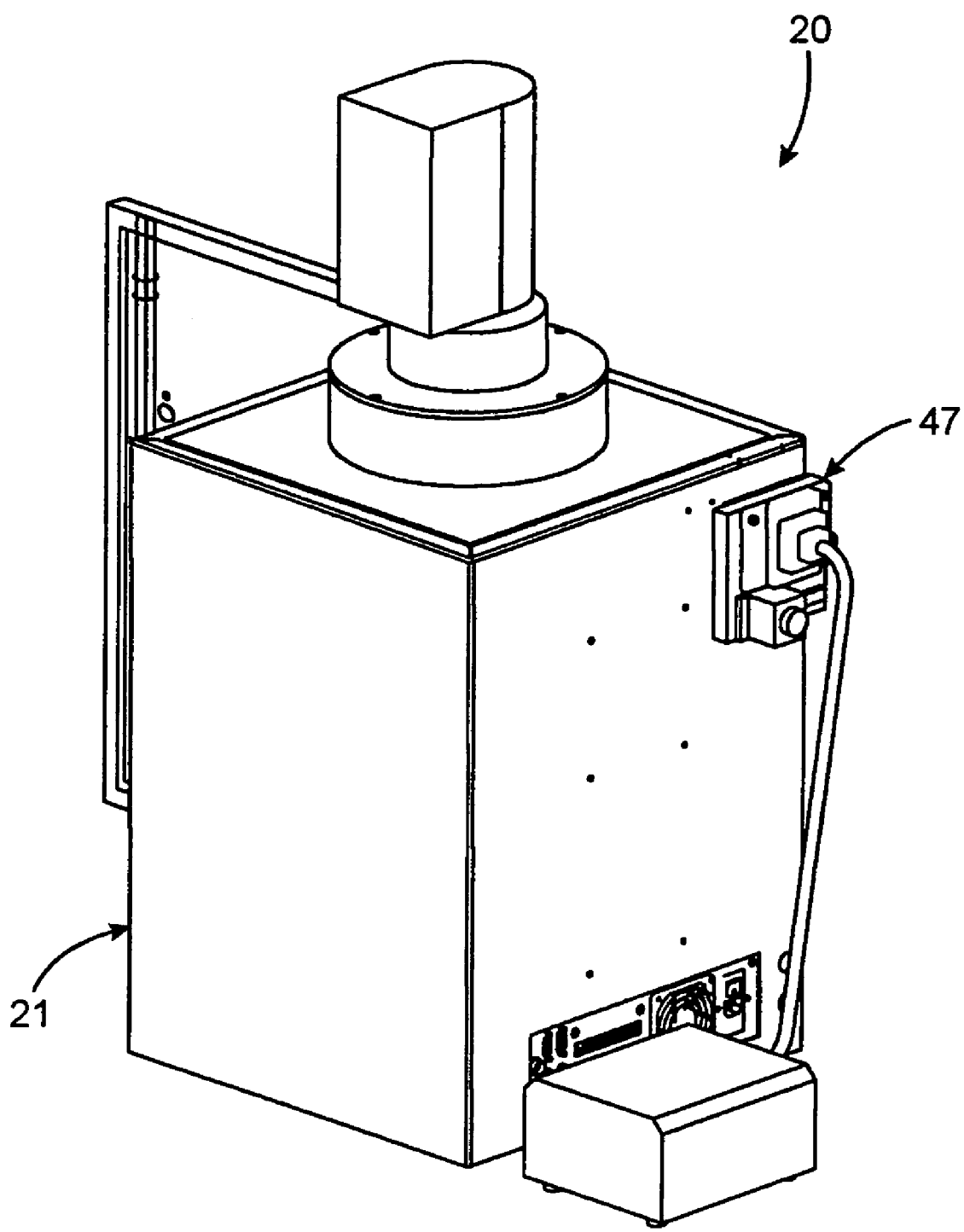
FIG. 18 is a rear perspective view of a light source and a filter wheel assembly of the illumination assembly of FIG. 12 optically coupled to the imaging apparatus.
Figure 19:
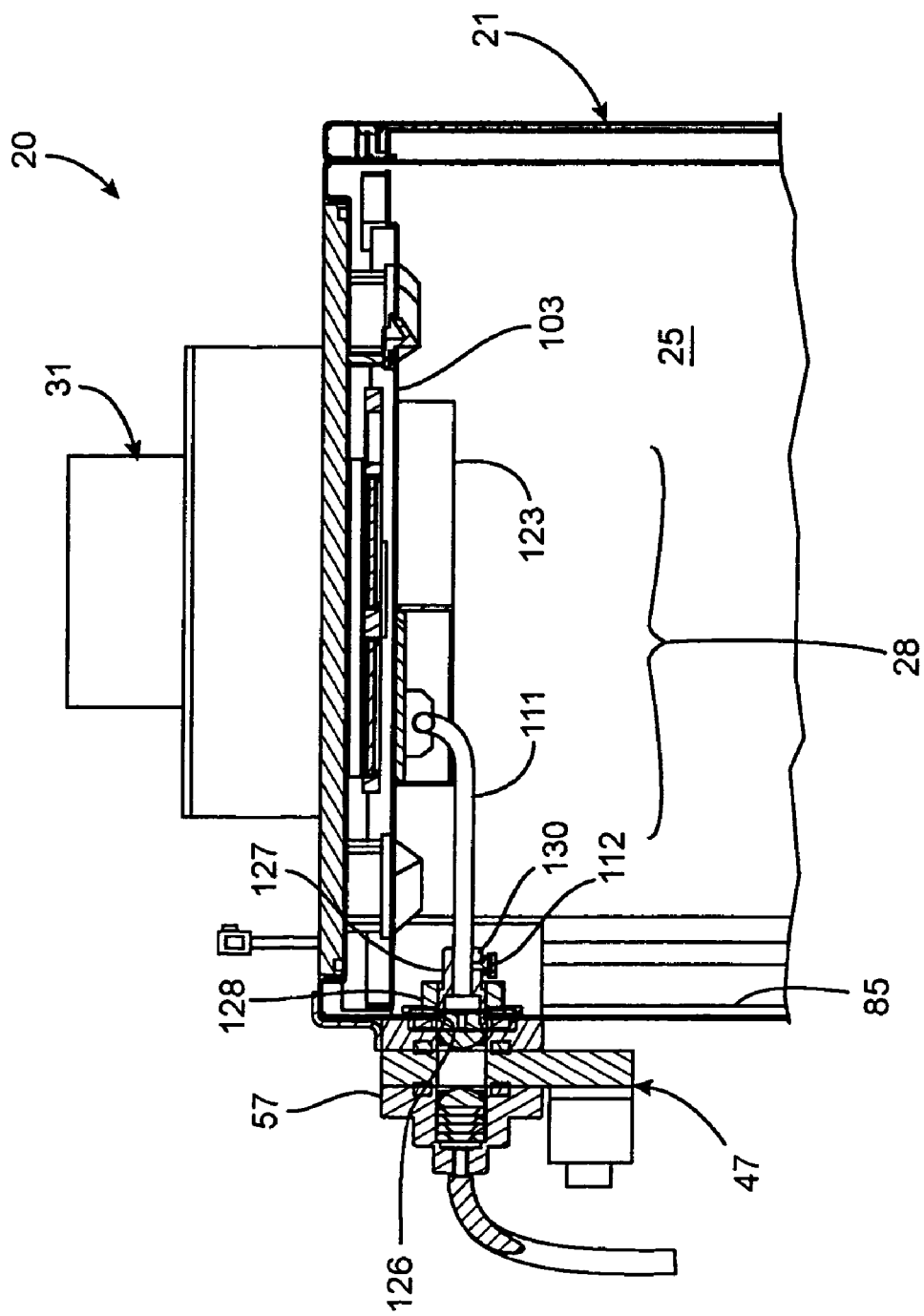
FIG. 19 is an enlarged, side elevation view, in cross-section, of the filter wheel assembly of the illumination assembly mounted to the imaging apparatus of FIG. 18.

As shown in FIGS. 18 and 19, the filter assembly 47 may include a mounting bracket (not shown) which affixes the housing 57 to one wall of the imaging apparatus. The side wall 85 of the housing 57 includes a passage 126 sized for sliding receipt of the downstream connector portion 127 of the filter housing 57 there through. A threaded nut 128 may also be provided which is fastened from inside the imaging chamber 25 to affix the filter assembly 47 to the imaging apparatus. The proximal connector end 130 of the fiber optic bundle 111 can then be removably attached to the downstream connector portion.

This arrangement is particularly suitable for this application since the length of the fused silica clad silica fiber optic bundle can be minimized. In effect, the path length of the filtered light passing through the fused clad silica fiber optic bundle is reduced significantly to minimize any auto fluorescence thereof, even though such material already has low auto fluorescence properties. Moreover, high purity or substantially pure fused clad silica is very expensive, and minimizing the length of the bundle ultimately reduces costs.

Referring now to FIGS. 20–24, in still another aspect of the present invention, an alternative embodiment macroscopic fluorescence illumination assembly, generally designated 140, is provided for use with the imaging apparatus 21. In this configuration, a bottom illumination configuration is provided that significantly reduces background fluorescent or autofluorescent signals emitted from the endogenous animal tissue itself. Briefly, this is one of the most significant limitations to fluorescent imaging contrast. Biological tissues have an inherent fluorescent signal that is strongly excited by excitation light that is in the blue/green region of the spectrum. These autofluorescent signals limit the sensitivity of detection by reducing the signal to background of the desired fluorescent labeling reagent.

There are several techniques that can reduce this background fluorescent signal, one of which includes moving the excitation light source wavelength towards the infrared region of the spectrum. In this region, the tissue autofluorescence is reduced, but not totally eliminated. The drawback to this technique is that it is not always feasible to use an infrared dye which would be necessary. Another approach to minimize the tissue autofluorescence signal from the sample is to alter the illumination configuration. The illumination design in the above-mentioned configuration is that of a front illumination profile, sometimes referred to as top illumination, where the excitation light source in the fluorescent kit and the detection equipment (i.e., camera 31) are on the same side of the specimen. Since the excitation light intensity is highest on the side of the specimen facing the camera 31, the tissue autofluorescent signal emitted is also highest on this side. Thus, the ratio of the signal to background noise of the desired fluorescent labeling reagent is significantly reduced, limiting the sensitivity of detection by the camera.

In accordance with the bottom illumination assembly design of the present invention, the excitation light source is located on the opposite side of the specimen as the detection system. Generally referred to as transillumination or bottom illumination, this illumination configuration reduces the autofluorescent signal from the sample by trapping the autofluorescent light on the opposite or bottom side of the animal relative to the camera.

Figure 20:
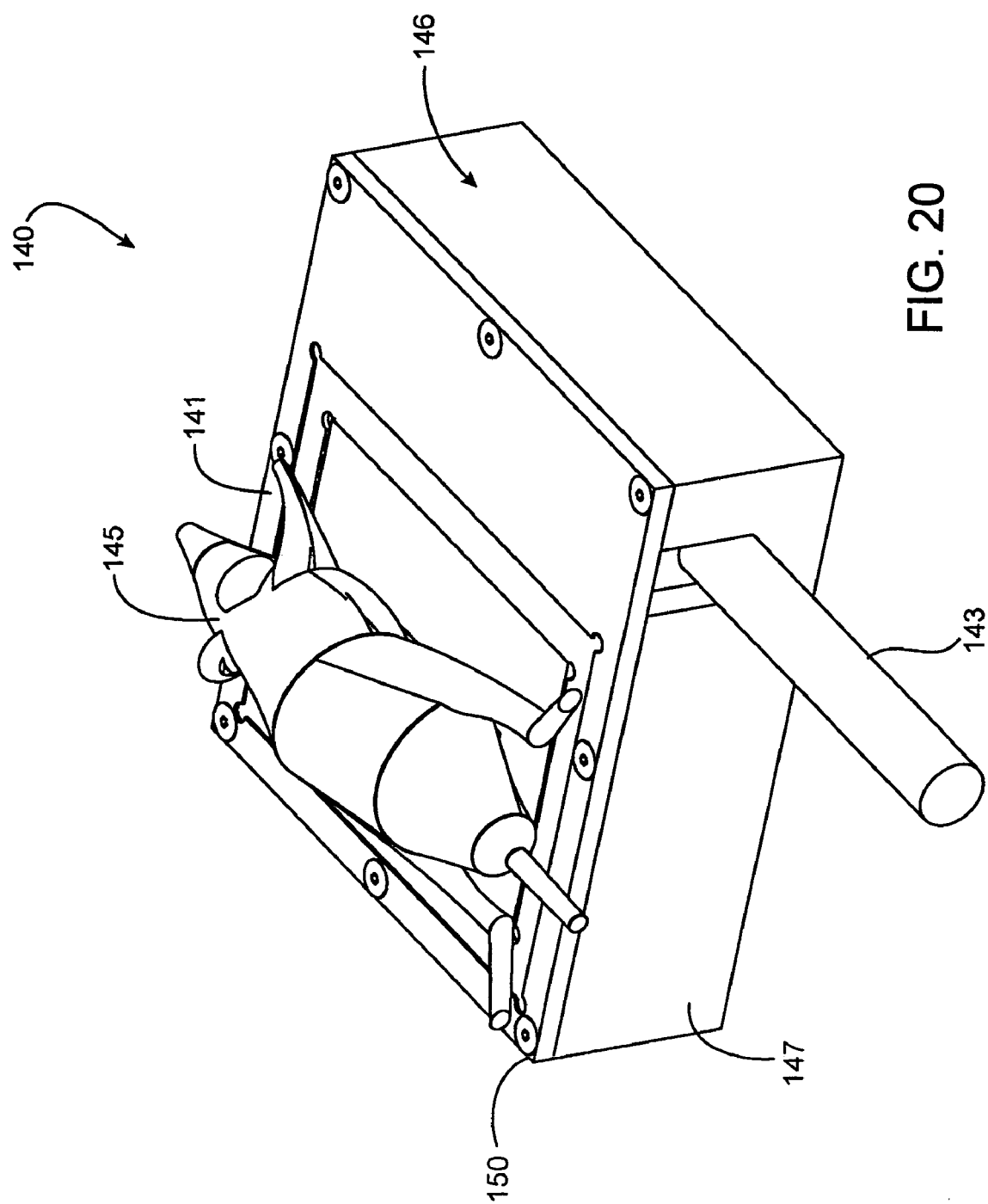
FIG. 20 is a top perspective view of an alternative embodiment bottom illumination assembly providing bottom illumination of the specimen constructed according to the present invention.
Figure 21:
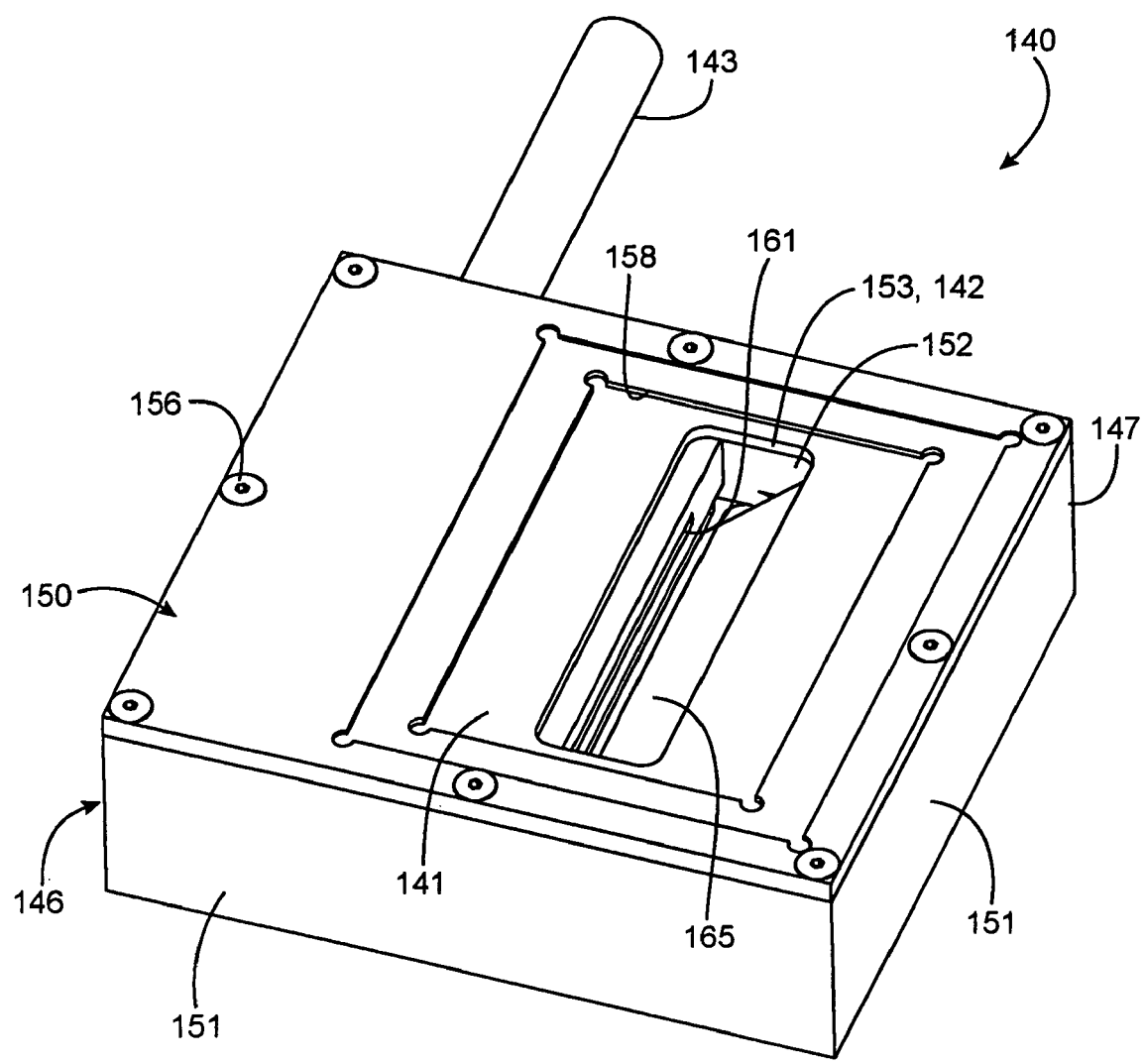
FIG. 21 is an enlarged, top perspective view of the bottom illumination assembly of FIG. 20 without the specimen thereatop.
Figure 23:
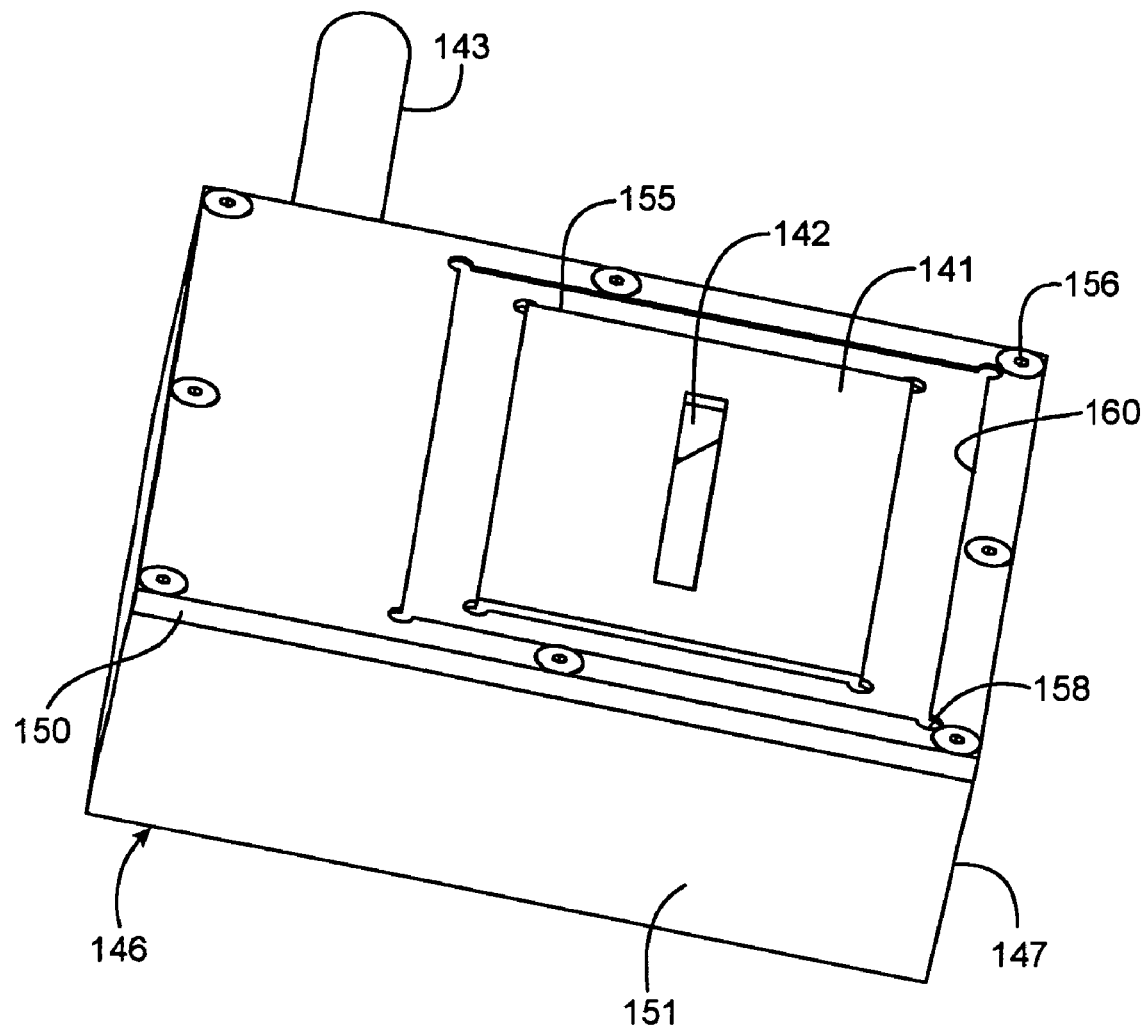
FIG. 23 is an enlarged, top perspective view of the bottom illumination assembly of FIG. 20 with a slide device positioned thereatop.

Referring to FIGS. 20, 21 and 23, the bottom side illumination assembly 140 is shown including a specimen support surface 141 sized and dimensioned for receipt in the imaging compartment 25 atop the specimen platform 26 of the imaging apparatus 21 (e.g., as shown in FIG. 1). The support surface 141 is substantially opaque and defines a window portion 142 that enables the passage of light there through which is oriented to face toward the view port 23 thereof. The window portion is selectively sized and dimensioned such that when the specimen is supported atop the support surface 141, it can be positioned and seated fully over the window portion in a manner forming a light-tight seal substantially there between. The illumination assembly 140 further includes an excitation light source 37, and a bundle of fiber optic strands 143 having proximal ends thereof in optical communication with the light source 37. The distal ends of the strands terminate proximate the window portion of the support surface. The distal ends each emit a respective beam of light originating from the light source 37 which are then collectively directed toward the window portion 142 and into a bottom side of the specimen 145.

Accordingly, since biological tissue is a turbid medium, the excitation light entering the specimen becomes multiply scattered and diffused where it propagates throughout the entire specimen, thereby exciting the fluorophore. The fluorophore emission is also scattering by tissue, and eventually, some of the scattered excitation light exits the topsides of the specimen 145, and is captured through the view port 23 and into the camera 31.

In one specific configuration, the bottom illumination assembly 140 includes a specimen illumination platform, generally designated 146, having a support structure 147 and a cover plate 150 removably mounted atop the support structure. The support structure 147 is preferably rectangular shaped having four upstanding side walls 151 surrounding an interior cavity 152 thereof. The support structure 147 is preferably substantially rigid, and may be fabricated from one or more pieces of black anodized aluminum, however, to reduce auto fluorescence. Other rigid materials may be applied, as noted above. The interior surface of the upstanding walls 151 are preferably coated with a material which absorbs light, such as black anodize, or is composed of opaque materials having absorption properties, such as black Delrin. It will further be appreciated, of course, that the support structure can be other shapes as well.

Mounted atop the upper edges of the upstanding walls 151 is the cover plate 150 that incorporates the support surface 141 to support the specimen 145. The cover plate 150 is also preferably composed of a rigid material such as black anodized aluminum to reduce autofluorescence. The peripheral footprint of the cover plate is rectangular, and is sized to match that of the support structure 147 when mounted thereto. A plurality of set screws 156 (eight as shown) cooperate with aligned screw holes 157', 157 (FIG. 24) in the respective cover plate 150 and support structure 147 to removably mount the two together. A gasket or the like may be provided between the interface to assure a light-tight seal there between.

Extending through the cover plate from the support surface 141 to a bottom side is an aperture 153 that enables the excitation light to pass from the interior cavity 152, and into the specimen. Thus, in some configurations, the aperture 153 functions as the window portion 142 of the support surface 141. This aperture is preferably rectangular shaped, but can be any size and/or shape to better coordinate with the shape of the specimen supported over the aperture. When the aperture 153 functions as the window portion, the specimen must be large enough to form a light-tight seal all around the edge of the aperture 153 when it is properly seated atop the support surface 141. Thus, essentially, the peripheral footprint of the aperture 153 must be sufficiently smaller than that of the properly oriented specimen 145 to form such a seal. It will be understood that without the formation of this light-tight seal between of the specimen with the edge defining the aperture, unscattered excitation light would leak into the imaging compartment 25 of the imaging apparatus 21 and be detected by the sensitive camera 31.

In one specific example, the opening (i.e., window portion 142) upon which light may pass through from the interior cavity 152 of the specimen illumination platform 146, and into the specimen can be sized and dimensioned to assure the formation of such a light-tight seal. This may be performed by providing a removable slide device 155 (FIGS. 23 and 24) or the like that is sized for aligned positioning into a receiving slot 158 formed in the support surface 141 of the cover plate 150. This receiving slot 158 is generally rectangular shaped, and is of a height profile such that when the slide device 155 is received in the receiving slot 158, the top surface of the slide device 155 is substantially flush with the top surface of the cover plate 150, thus becoming the support surface 141.

Figure 24:
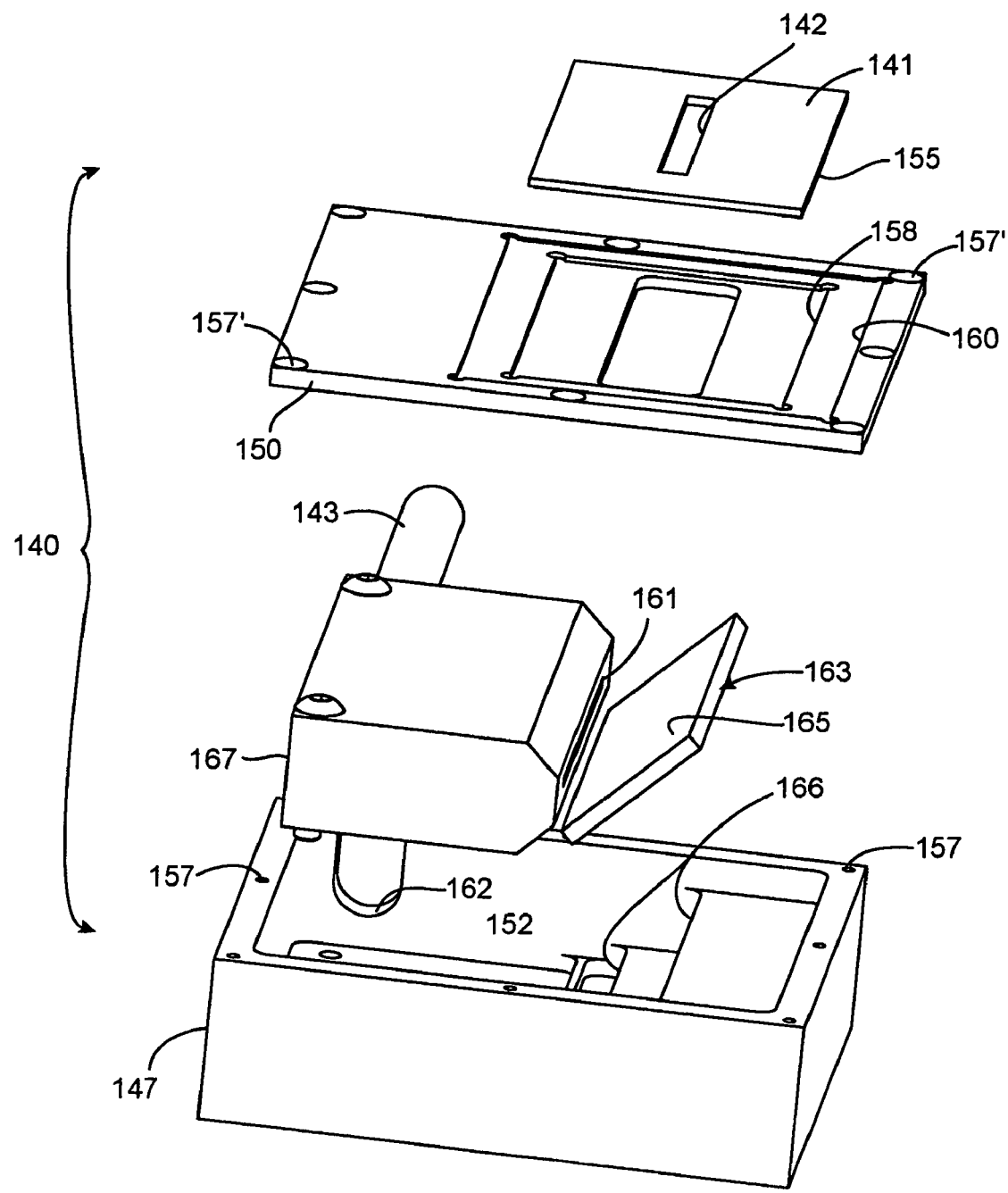
FIG. 24 is an exploded top perspective view of the bottom illumination assembly of FIG. 20.

The slide device 155 is preferably formed of a transparent material, such as a glass slide, sized and dimensioned for receipt in the receiving slot 158 (FIGS. 21 and 24). By painting the top or bottom side of the glass with an opaque paint material, such as Krylon black paint, the transparent window portion 142 that permits the passage of the excitation light into the specimen can be formed from a void in the painted surface. Using a plurality or set of slide devices 155, a variety of different size and shape window portions 142 can be provided. Accordingly, the size of the window portion 142 can be altered by merely changing the slide device 155. As mentioned, should the specimen have a footprint large enough, the slide device 155 can be removed altogether and the specimen be placed directly atop and over the aperture 153.

To assure cleanliness of the slide device 155, a disposable lining (not shown) may be included which is positioned atop the support surface 141 of the slide device. This disposable lining, which may be composed of paper, is preferably dimensioned to seat into and along the peripheral lining edge 160 surrounding the receiving slot 158 of the cover plate 150. This lining edge performs the function of aligning and seating the disposable lining, similar to that between the receiving slot 158 and the slide device 155. The lining includes an opening larger than the window portion 142 of the slide device 155 so as not to obstruct the passage of excitation light into the specimen.

Similar to the top illumination configuration above-mentioned, the bottom illumination assembly 140 includes a bundle 143 of fiber optic strands composed of materials selected to have low autofluorescence properties. Again, one material particularly suitable for the fiber optic strands and filters is high purity fused silica, such as plastic clad fused silica or silica clad fused silica, which has very low autofluorescence. Further, as indicated above, all exterior fiber optic bundle portions of the fiber optic bundle 35 include a segmented, flexible metal jacket (not shown) placed around these portions together with an exterior flexible PVC sleeve 42 to reduce the introduction of exterior light or noise into the fiber optic strands. This sleeve is opaque (black), and blocks all external ambient light that might enter the fiber bundle.

The fiber optic bundle portions internal to the imaging box are surrounded by a non-phosphorescent material to substantially eliminate the possibility of spurious light sources from the fiber optic bundle within the imaging box. One particular flexible material which has low phosphorescence is a polyolefin heat shrink tubing material. Again, all optical filters (e.g., interference-type filters including bandpass filters, longpass filters and shortpass filters), filter wheel assemblies, illumination sources, fiber optic connections external to and into the imaging apparatus 21 are similar to that discussed above. Further, while the composition of the fiber optic strands for the internal fiber optic bundle may be composed of fused silica, as mentioned above, they are preferably composed of conventional fiber optic glass. Relatively costly fused silica has lower autofluorescence properties, but this is not as critical for bottom illumination where the autofluorescence is trapped under the specimen where it is not detected or seen by the camera.

In this specific embodiment, the bundle of fiber optic strands for the bottom illumination assembly 140 originates from an interior side wall 85 of the imaging apparatus 21 similar to the top illumination assemblies such as the light-ring embodiment above. In the bottom illumination assembly 140, however, the optical connector into the imaging apparatus 21 may be positioned lower to the bottom specimen platform 26 so that the bundle of fiber optic strands can extend into the interior cavity 152 of the support structure 147 without being significantly bent.

Figure 22:
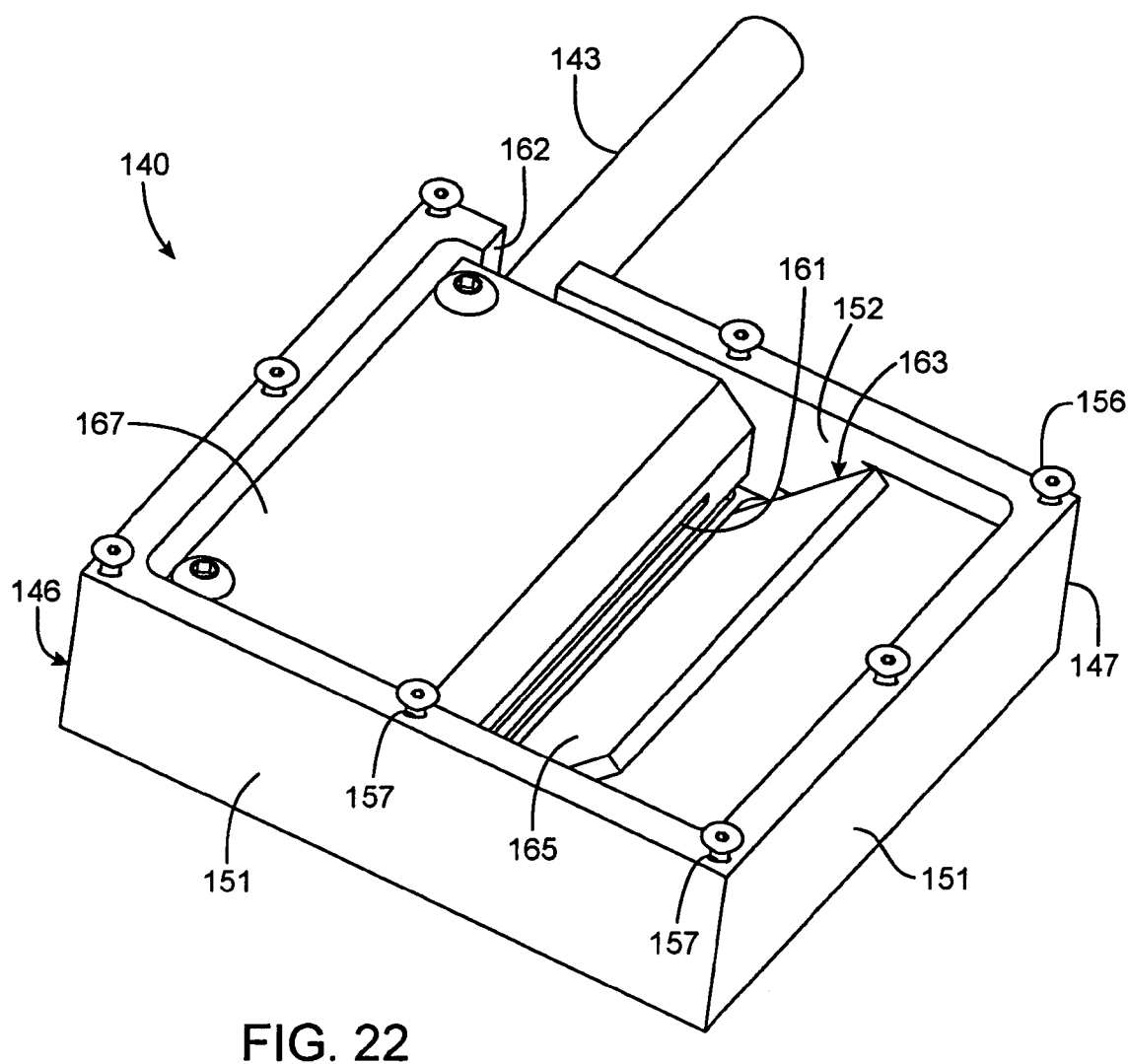
FIG. 22 is an enlarged, top perspective view of the bottom illumination assembly of FIG. 20 with the cover plate removed.

FIGS. 22 and 24 best illustrates that the distal ends 161 of the fiber optic bundle 143 terminate in the interior cavity 152 of the specimen illumination platform 146. A bundle slot 162 is provided in one of the upstanding walls 151 of the support structure 147 for receipt of the fiber optic bundle portion 143 there through. In one configuration, the distal ends 161 of the fiber strands of the fiber optic bundle 143 are oriented to direct the conical beams of light emitted there from directly through the window portion 142 and into the specimen seated thereatop.

Similar to the dispersion assembly 110 of the top illumination assembly above, a reflector device 163 is included in the interior cavity 152 of the support structure 147 that is configured to cooperate with the distal ends 161 of the fiber optic strands to redirect the directional beams collectively through the window portion 142 of the slide device 155. Accordingly, the optical axes of the distal ends 161 of the fiber optic strands may be retained generally parallel to the horizontal plane of the fiber optic bundle portion extending through the bundle slot 162 and into the interior cavity 152 of the support structure 147, while the directional beams emitted from the strand distal ends are reflected (E.g., through reflector device 163) upwardly through the window portion 142 and into the specimen 145. The overall height of the bottom illumination assembly 140 can, thus, be significantly reduced since the distal ends of the fibers themselves need not be curved upward toward the window portion.

The reflector device 163 includes a reflective surface 165 oriented at an angle about 45° relative the direction substantially parallel to the optical axes of the distal ends of the fiber optic strands to reflect the directional beams of light about 90° from that emitted from the distal ends. To orient the reflector device 163 properly relative the distal ends 161 of the fiber optic bundle, mounting supports 166 are provided in the interior cavity 152 of the support structure upon which a backside of the reflector device seats. The reflector device 163 is then either permanently seated against the mounting supports through an adhesive, or removably mounted to permit interchangeability of the reflector device.

The reflective surface 165 is preferably mirror-like for non-diffuse reflection of the excitation light fully into the bottom side of the specimen. In this configuration, the turbid medium of the biological tissue is relied upon to multiply scatter and uniformly propagate the excitation light though the entire specimen. In other configurations, the reflective surface 165 may include a diffuse material that diffuses the light reflected through the window portion 142. As mentioned above, these diffuser materials may include a roughed aluminum surface or SPECRALON®.

The reflective surface 165 is preferably substantially planar. It is conceivable, however, that the reflective surface could be partially concave to reflectively focus the reflected excitation light toward a smaller area or through discretely shaped window portions. This would be particularly valuable should the size and shape of the window portion be smaller than the size and shape of the layout distribution of the distal ends of the fiber optic bundle. In the configuration shown in FIGS. 22 and 24, however, the reflective surface 165 is preferably rectangular-shaped. Both the reflective surface 165 and the layout distribution of the distal ends of the fiber optic bundle, as will be described, are sized and dimensioned to match one another. Accordingly, both the reflective surface and the layout distribution of the distal ends of the fiber optic bundle 143 are elongated and rectangular-shaped (i.e., conforming to the rectangular-shaped aperture 153 and window portion 142).

As shown, the distal ends of said fiber optic bundle are thus aligned in a linear array extending substantially along the elongated reflective surface 165. Preferably, the distal ends 161 in the fiber optic cable are rearranged from a round bundle (about 0.7cm in diameter) to a line or an elongated rectangle array of fibers that is approximately 6 cm long and 0.2 cm wide. One example of a round to linear fiber cable is the distribution unit 167 that commercially available from Dolan Jenner Industries of Lawrence, Mass., model no. BL405. In this example, the interior cavity 152 of the support structure 147 is sized to slideably receive the rectangular housing of the distribution unit 167 in a manner automatically aligning and spacing the distal ends 161 along and relative to the reflector device 163.

Although only a few embodiments of the present inventions have been described in detail, it should be understood that the present inventions may be embodied in many other specific forms without departing from the spirit or scope of the inventions.

What is claimed is:

1. A macroscopic fluorescence illumination assembly for use with an imaging apparatus defining a light-tight imaging compartment, said imaging apparatus including an interior wall defining a view port extending into said imaging compartment to enable viewing of a specimen contained in said imaging compartment, said illumination assembly comprising:

a specimen support surface configured for positioning in said imaging compartment in a manner oriented to face toward said view port of the imaging apparatus, said support surface defining a window portion enabling the passage of light there through, said window portion being selectively sized and dimensioned such that the specimen, when supported atop the support surface, is positioned and seated over said window portion in a manner forming a light-tight seal substantially there between; and an illumination device directing light toward said window portion and into a bottom side of said specimen wherein the diffused light exits a topside thereof for receipt through said view port to view the fluorescence of said specimen.

2. The illumination assembly as defined by claim 1, wherein said illumination device includes a light transmission unit having a proximal end thereof in optical communication with an excitation light source and a distal end thereof terminating proximate said window portion of the support surface, said distal end emitting said light in a beam toward said window portion.

3. The illumination assembly as defined by claim 2, wherein said light transmission unit includes a bundle of fiber optic strands.

4. The illumination assembly as defined by claim 3, wherein said excitation light source is a fluorescent light source.

5. The illumination assembly as defined by claim 2, further including:

an opaque cover plate providing said support surface, and a support structure cooperating with the cover plate to define a light-tight interior cavity below the window portion.

6. The illumination assembly as defined by claim 2, further including:

a reflector device cooperating with the light emitted from the distal end of the transmission unit to reflect the same through said window portion of the support surface.

7. The illumination assembly as defined by claim 6, wherein a substantially parallel optical axis of the distal end of the transmission unit is oriented substantially perpendicular to a plane containing said window portion of the support surface; and said reflector device includes a substantially planar reflective surface oriented at an angle about 45° relative the direction substantially parallel to the optical axis of the distal end of the transmission unit to reflect the directional beams of light emitted there from through said window portion.

8. The illumination assembly as defined by claim 7, wherein said reflective surface includes a diffuser material to diffuse the light toward said window portion in a substantially uniform manner.

9. The illumination assembly as defined by claim 5, further including
a plurality of cover plates, each having a support surface defining a different area window portion, and each being adapted for removable mounted to said support structure.

10. A macroscopic fluorescence imaging assembly for viewing a specimen comprising:
an imaging apparatus having an enclosure wall defining a view port into a light-tight imaging compartment containing the specimen thereof;
a specimen illumination platform contained in said imaging compartment having a support surface facing toward said view port, said support surface defining a window portion enabling the passage of excitation light there through, said window portion being selectively sized and dimensioned such that the specimen, when supported atop the support surface, is positioned and seated over said window portion in a manner forming a light-tight seal substantially there between such that when excitation light is transmitted through window portion and into a bottom side of said specimen, the diffused excitation light exits a topside thereof for receipt through said view port to view the fluorescence of said specimen.

11. The imaging assembly as defined by claim 10, further including:
an illumination device providing said excitation light.

12. The imaging assembly as defined by claim 11, wherein said illumination device includes a light transmission unit having a proximal end thereof in optical communication with an excitation light source and a distal end thereof terminating proximate said window portion of the support surface, said distal end each said excitation light originating from said light source which is directed toward said window portion and into the bottom side of said specimen.

13. The imaging assembly as defined by claim 12, further including:
an excitation interference filter positioned in the path of the transmission unit to filter the light passing there through.

14. The imaging assembly as defined in claim 13, further including:
a filter housing containing the interference filter therein in a substantially light-tight recess, and
a collimating lens disposed in said housing between the transmission end of the transmission unit and said upstream side of the interference filter to collimate substantially all of the light passing there through.

15. The imaging assembly as defined by claim 10, wherein
said specimen illumination platform includes a cover plate providing said support surface.

16. The imaging assembly as defined by claim 10, further including:
a camera mounted to the enclosure and having a lens optically extending through said view port to capture illuminated specimen images on the specimen illumination platform.

* * * * *